(12) United States Patent
Ahmadi et al.

(10) Patent No.: US 10,548,523 B2
(45) Date of Patent: Feb. 4, 2020

(54) PRESSURE SENSING CATHETER SYSTEM

(71) Applicant: REGENTS OF THE UNIVERSITY OF MINNESOTA, Minneapolis, MN (US)

(72) Inventors: Mahdi Ahmadi, Minneapolis, MN (US); Rajesh Rajamani, Saint Paul, MN (US); Gerald Timm, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 484 days.

(21) Appl. No.: 14/681,476

(22) Filed: Apr. 8, 2015

(65) Prior Publication Data

US 2015/0282753 A1 Oct. 8, 2015

Related U.S. Application Data

(60) Provisional application No. 61/976,919, filed on Apr. 8, 2014.

(51) Int. Cl.
| | | |
|---|---|---|
| *A61B 5/20* | (2006.01) | |
| *A61B 5/0492* | (2006.01) | |
| *A61B 5/0488* | (2006.01) | |
| *A61B 5/00* | (2006.01) | |

(52) U.S. Cl.
CPC ............ *A61B 5/205* (2013.01); *A61B 5/0492* (2013.01); *A61B 5/04882* (2013.01); *A61B 5/6853* (2013.01); *A61B 5/7203* (2013.01); *A61B 2560/0261* (2013.01); *A61B 2562/0214* (2013.01); *A61B 2562/0247* (2013.01); *A61B 2562/043* (2013.01); *A61B 2562/063* (2013.01)

(58) Field of Classification Search
CPC ... A61B 5/205; A61B 5/04882; A61B 5/0492; A61B 5/6853; A61B 2562/0214; A61B 2562/0261; A61B 2562/0247; A61B 2562/043; A61B 2562/063
USPC ......................................................... 600/301
See application file for complete search history.

(56) References Cited

U.S. PATENT DOCUMENTS

| | | |
|---|---|---|
| 4,063,548 A | 12/1977 | Klatt et al. |
| 4,191,196 A | 3/1980 | Bradley et al. |
| 4,233,991 A | 11/1980 | Bradley et al. |

(Continued)

FOREIGN PATENT DOCUMENTS

| | | |
|---|---|---|
| CN | 202223608 U | 5/2012 |
| CN | 202235374 U | 5/2012 |

(Continued)

OTHER PUBLICATIONS

Flexible Tactile Sensor for Tissue Elasticity Measurements, Peng et al., Journal of Microelectromechanical Systems, vol. 1, No. 6, Dec. 2009 (8 pages).

(Continued)

*Primary Examiner* — Paula J Stice
(74) *Attorney, Agent, or Firm* — Dicke, Billing & Czaja PLLC

(57) ABSTRACT

A pressure sensing catheter system includes a urethral catheter and a sensor array formed on the urethral catheter. The sensor array includes a plurality of pressure sensors distributed along a length of the urethral catheter. The sensor array is configured to produce a dynamic pressure distribution profile along a urethra.

20 Claims, 24 Drawing Sheets

(56) References Cited

U.S. PATENT DOCUMENTS

| | | | |
|---|---|---|---|
| 4,248,214 | A | 2/1981 | Hannah et al. |
| 4,710,169 | A | 12/1987 | Christopher |
| 4,850,358 | A | 7/1989 | Millar |
| 4,873,990 | A | 10/1989 | Holmes et al. |
| 4,932,948 | A | 6/1990 | Kemes et al. |
| 5,423,329 | A | 6/1995 | Ergas |
| 5,593,389 | A | 1/1997 | Chang |
| 6,083,179 | A | 7/2000 | Oredsson |
| 6,602,243 | B2 | 8/2003 | Noda |
| 8,602,897 | B2 | 12/2013 | Addington et al. |
| 9,078,570 | B2 * | 7/2015 | Parks ............... A61B 5/037 |
| 2002/0139419 | A1 | 10/2002 | Flinchbaugh |
| 2003/0033886 | A1 * | 2/2003 | Davie ............... F16K 41/02 73/780 |
| 2006/0254369 | A1 * | 11/2006 | Yoon ............... A61B 5/6804 73/862.041 |
| 2007/0225616 | A1 * | 9/2007 | Brown ............... A61B 5/0006 600/587 |
| 2007/0293792 | A1 * | 12/2007 | Sliwa ............... A61B 5/11 600/587 |
| 2008/0094610 | A1 | 4/2008 | Muller |
| 2008/0221598 | A1 * | 9/2008 | Dlugos ............... A61F 5/005 606/157 |
| 2009/0036754 | A1 * | 2/2009 | Pons ............... A61B 5/02156 600/301 |
| 2009/0048488 | A1 * | 2/2009 | Uchimura ............ A61B 1/0052 600/152 |
| 2009/0318757 | A1 | 12/2009 | Singh |
| 2010/0057046 | A1 * | 3/2010 | Stevens (nee Webber) ............... A61B 5/02055 604/507 |
| 2013/0184567 | A1 | 7/2013 | Xie et al. |
| 2014/0296687 | A1 * | 10/2014 | Irazoqui ............... A61B 3/16 600/398 |

FOREIGN PATENT DOCUMENTS

| | | |
|---|---|---|
| DE | 4111961 A1 | 10/1992 |
| JP | H01284267 A | 11/1989 |
| WO | 2006083680 A1 | 8/2006 |

OTHER PUBLICATIONS

Good Urodynamic Practices: Uroflowmetry, Filling Cystometry, and Pressure-Flow Studies, Schafer et al; Neurourology and Urodynamics 21:261-274, © 2002 Wiley-Liss, Inc. (14 pages).

The Impact of Multichannel Urodynamics Upon Treatment Recommendations for Female Urinary Incontinence, Ward et al., Published Apr. 19, 2008 © International Urogynecology Journal 2008 (7 pages).

Novel MEMS Stiffness Sensor for Force and Elasticity Measurements, Peng et al., Sensors and Actuators A: Physical, © Elsevier B.V. Dec. 2009 (8 pages).

Piezoelectric MEMS Sensors: State-of-the-Art and Perspectives, S. Tadigadapa et al., Measurement and Technology, © 2009 IOP Publishing Ltd. (31 pages).

An Ultraminiature Mems Pressure Sensor With High Sensitivity for Measurement of Intramuscular Pressure (IMP) in Patients With Neuromuscular Diseases, A.S. Sezen et al., Journal of Medical Devices, Sep. 2009, vol. 3, © 2009 by ASME (9 pages).

Urodynamic Changes Induced by the Intravaginal Electrode During Pelvic Floor Electrical Stimulation, Julio Resplande et al., Neurology and Urodynamics 22:24-28, © 2003 Wiley-Liss, Inc. (5 pages).

Use of Urodynamics Prior to Surgery for Urinary Incontinence: How Helpful is Preoperative Testing? by Gary E. Lemack, Indian Journal of Urology Apr.-Jun. 2007; 23(2): 142-147, http://www.ncbi.nlm.nih.gov/pmc/articles/PMC2721523/ (8 pages).

MMS (Medical Measurement Systems), Luna—Catheters, accessed and printed Feb. 4, 2016, http://www.mmsinternational.com/int/761/urology-ambulatory-urodynamics-product-luna-catheters (1 page).

* cited by examiner

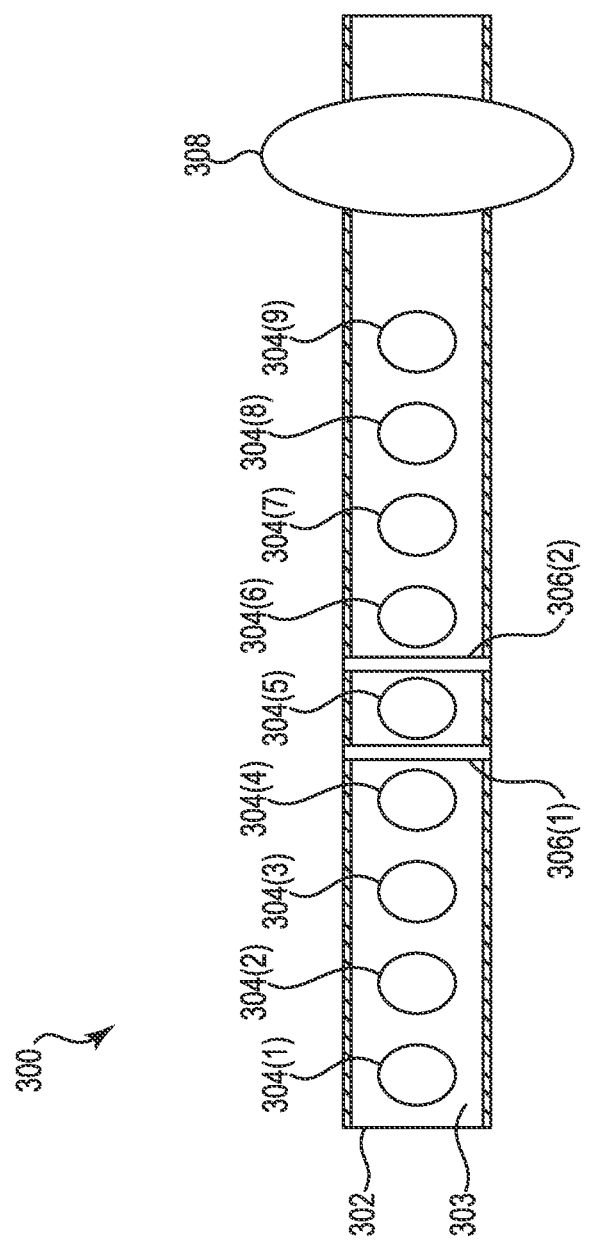

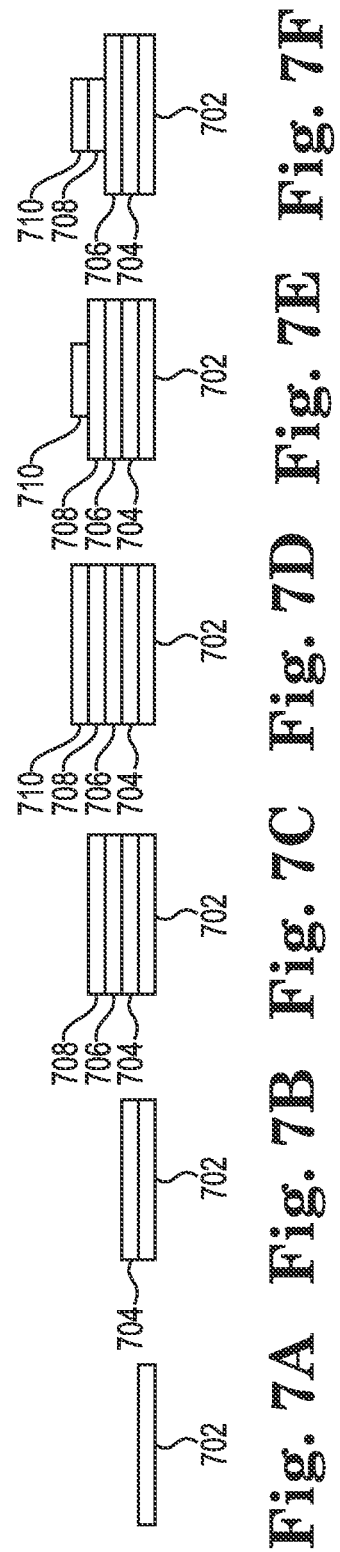

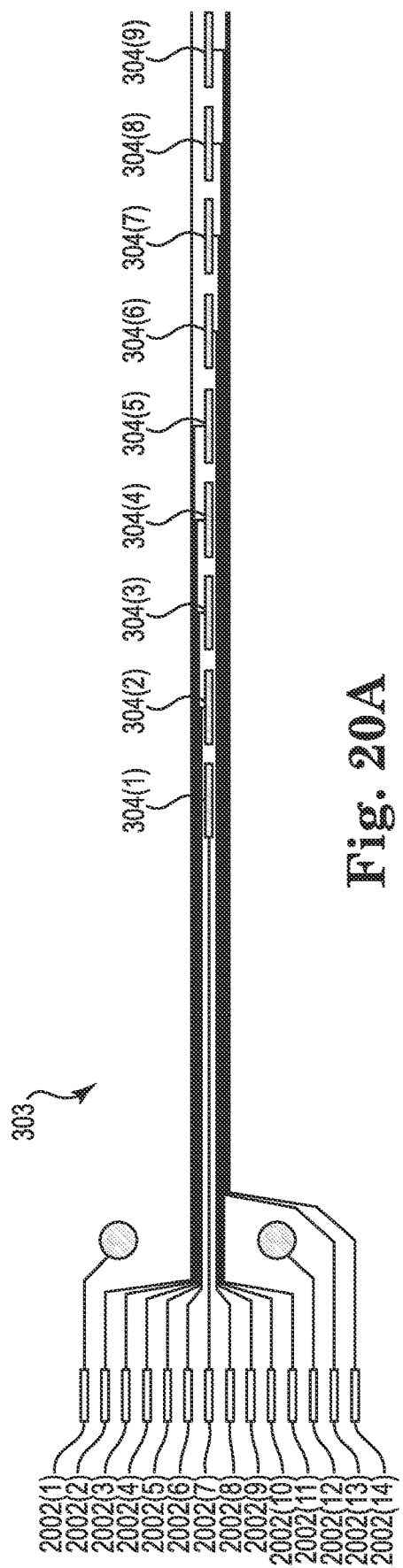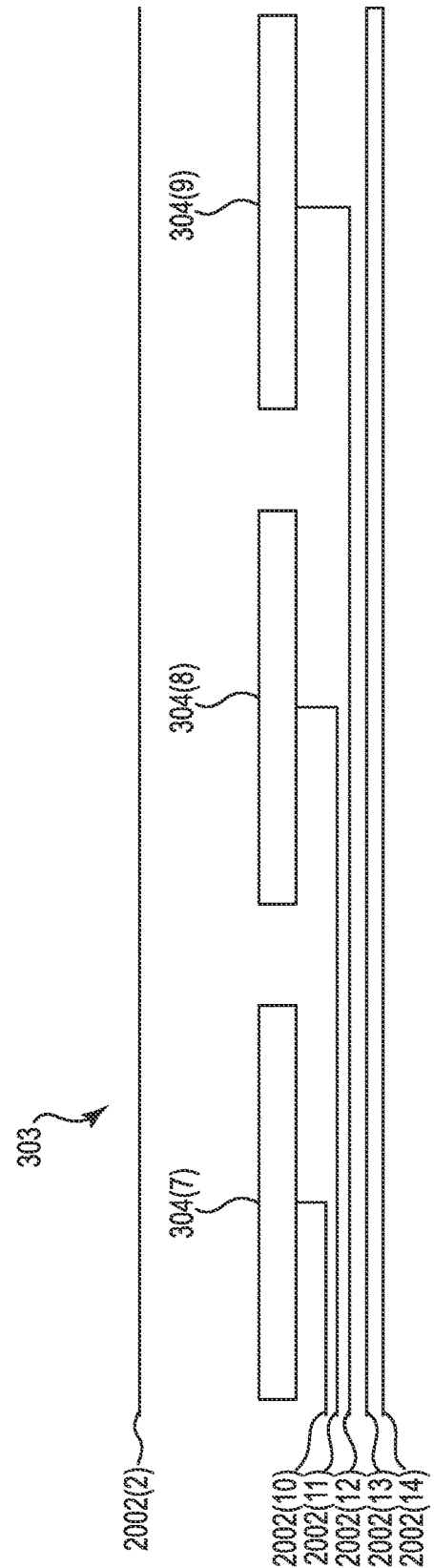
Fig. 20A
Fig. 20B

US 10,548,523 B2

PRESSURE SENSING CATHETER SYSTEM

CROSS-REFERENCE TO RELATED APPLICATIONS

This application claims priority under 35 U.S.C. § 119(e) to U.S. Provisional Patent Application Ser. No. 61/976,919 filed on Apr. 8, 2014, and incorporated herein by reference.

REFERENCE TO GOVERNMENT RIGHTS

This invention was made with government support under DK091555 awarded by the National Institutes of Health. The government has certain rights in the invention.

BACKGROUND OF THE INVENTION

Urinary incontinence (UI), as defined by the International Continence Society, is "the complaint of any involuntary leakage of urine." The most common type of urinary incontinence in women is stress urinary incontinence (SUI), followed by urge and mixed incontinence. Urinary incontinence is not a life-threatening or dangerous condition, but it is socially embarrassing and may cause withdrawal from social situations and reduced quality of life. An estimated 80% of people affected are women. Urinary incontinence is believed to affect at least 13 million people in the United States, and is expected to increase sharply with the aging of the baby boomers.

A variety of approaches have been designed to diagnose the cause of SUI. The most widely used method is urodynamics to measure storage and voiding functions of the urinary bladder and the urethra. Urodynamic testing normally consists of two main phases: 1) filling cystometry to investigate storage of urine in the bladder, including ability to store without leakage during provocative maneuvers such as coughs and in-spot jogging, and 2) followed by a pressure-flow measurement to examine urine voiding performance. During these tests, a thin, flexible catheter, called a Foley catheter, is inserted into the bladder through the urethra, and residual bladder volume is measured followed by the performance of filling, provocative and voiding studies. More sophisticated testing uses an intravaginal or peri-anal electrode to measure the electrical activity of the pelvic floor muscles. Further ambulatory urodynamic studies with natural filling are also applied for patients to avoid the unnatural environment of the urodynamic clinic. Ambulatory studies have been found useful for confirming overactive detrusor muscle activity in patients for whom conventional urodynamic tests failed to reproduce symptoms.

SUMMARY OF THE INVENTION

One embodiment is directed to a pressure sensing catheter system that includes a urethral catheter and a sensor array formed on the urethral catheter. The sensor array includes a plurality of pressure sensors distributed along a length of the urethral catheter. The sensor array is configured to produce a dynamic pressure distribution profile along a urethra.

BRIEF DESCRIPTION OF THE DRAWINGS

FIG. 3 is a diagram illustrating a pressure sensing catheter system that includes a Foley catheter with pressure and electromyography (EMG) sensors according to one embodiment.

FIGS. 7A-7F are diagrams illustrating a process for forming the capacitive sensors shown in FIG. 3 according to one embodiment.

FIG. 20A is a diagram illustrating signal lines of the sensor array according to one embodiment.

FIG. 20B is a diagram illustrating an expanded view of a proximal portion of the sensor array shown in FIG. 20A.

DETAILED DESCRIPTION OF THE INVENTION

Figure 1:
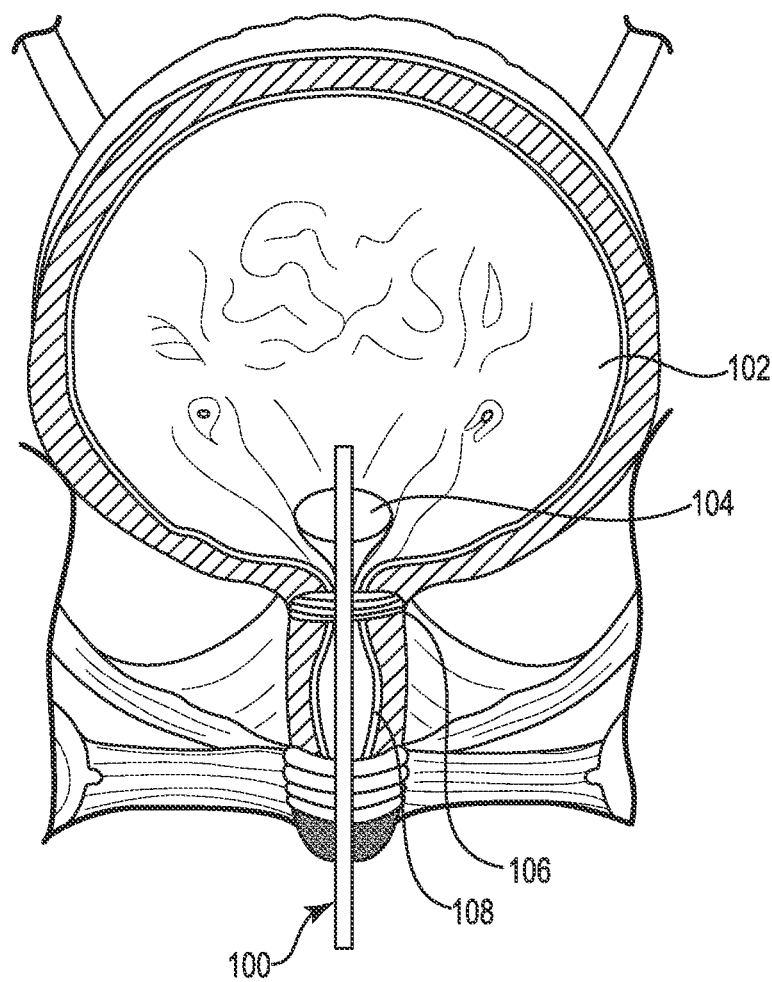
FIG. 1 is a diagram illustrating a Foley catheter for urodynamic measurements.

One embodiment is directed to a urethral catheter with a distributed micro-sensor strip (or sensor array) for improved urodynamics. The urethral catheter with the micro-sensor strip enables improved urodynamic diagnosis in subjects with urinary incontinence. The instrumented catheter can measure the dynamic pressure distribution profile along the urethra, which is not done with current urethral catheters. The pressure distribution measurements are combined with electromyography (EMG) measurements made on the same sensing strip to distinguish between neural and structural causes of urinary incontinence.

In one embodiment, the sensing strip is flexible in order to allow insertion into the male and female human urethra. Highly sensitive pressure sensors capable of measuring pressures as low as 0.1 psi are included on the strip. In one embodiment, the flexible sensing strip includes highly sensitive capacitive force sensors. The fabricated sensor strip according to one embodiment uses a flexible substrate, copper electrodes, polymer insulation, multi-layer design and assembly after alignment of the layers. Sensor readings can be disturbed by parasitic capacitance created by closeness to human tissues. In one embodiment, a reference sensor that measures parasitic capacitance but is immune to pressure influence is incorporated on the sensing strip to compensate for such disturbances. In-vitro experimental results show that good sensitivity and range are obtained using the sensor strip. Further, parasitics due to proximity to human tissues can be removed using the reference parasitic sensor to provide accurate urethral pressure values.

One embodiment is directed to a urodynamic catheter with a distribution of pressure sensors along its length together with an EMG recording electrode that can be positioned at the urogenital diaphragm. This makes possible the concurrent measurement of distributed urethral occlusive pressures with sphincter EMG during provocative maneuvers in a clinical environment.

In one embodiment, the catheter system includes a compact planar sensor strip that slides into a slot in the catheter and includes micro-sensors as well as embedded signal lines for sensor signal transmission to an external interface. The design allows unobstructed instrumentation of a urethral catheter with sensors to measure all of the variables described above.

The catheter according to one embodiment provides an ability to differentiate between structural and neurological causes of urinary incontinence. The catheter is configured to be positioned with the EMG electrodes at the site of maximum electrical activity corresponding with the site of the urogenital diaphragm muscles, peri-urethral striated muscles and urethral sphincter. Amplitude of EMG activity and distribution of occlusion pressures along the length of the urethra during filling and voiding of the bladder provides valuable information on the coordination of detrusor and sphincter muscle activity. Normally, detrusor contraction during voiding is accompanied by relaxation of the urethral sphincter to permit unobstructed voiding. Obstructed voiding due to elevated urethral occlusive pressure with absent EMG activity during detrusor contraction implies urethral constriction whereas elevated urethral occlusive pressure with elevated EMG activity implies detrusor/sphincter dyssynergia. Thus, structural and neurological causes can be differentiated. Urethral obstruction requires surgical correction while detrusor/sphincter dyssynergia is better managed with pharmacologic agents.

One embodiment is directed to a multi-sensor flexible catheter strip for measurement of distributed pressure in a human urethra. The sensor strip has important clinical applications in urodynamic testing for analyzing the structural and neural causes of urinary incontinence in patients. The sensor strip is highly sensitive and is flexible enough for urethral insertion into a human body, and works reliably in a liquid in-vivo environment in the human body. Capacitive force sensors for the sensor strip are designed and microfabricated using polyimide/PDMS substrates and copper electrodes. To remove the parasitic influence of urethral tissues which create fringe capacitance that can lead to significant errors, a reference fringe capacitance measurement sensor is incorporated on the strip.

FIG. 1 is a diagram illustrating a Foley catheter 100 for urodynamic measurements. The Foley catheter 100 is inserted into the urethra 108 of a patient until the distal end of the catheter 100 reaches the patient's bladder 102. An expandable balloon 104 is positioned at a distal end of the catheter 100, and may be inflated when positioned within the bladder 102 above the urethral sphincter 106 to help maintain the catheter 100 within the patient.

Figure 2:
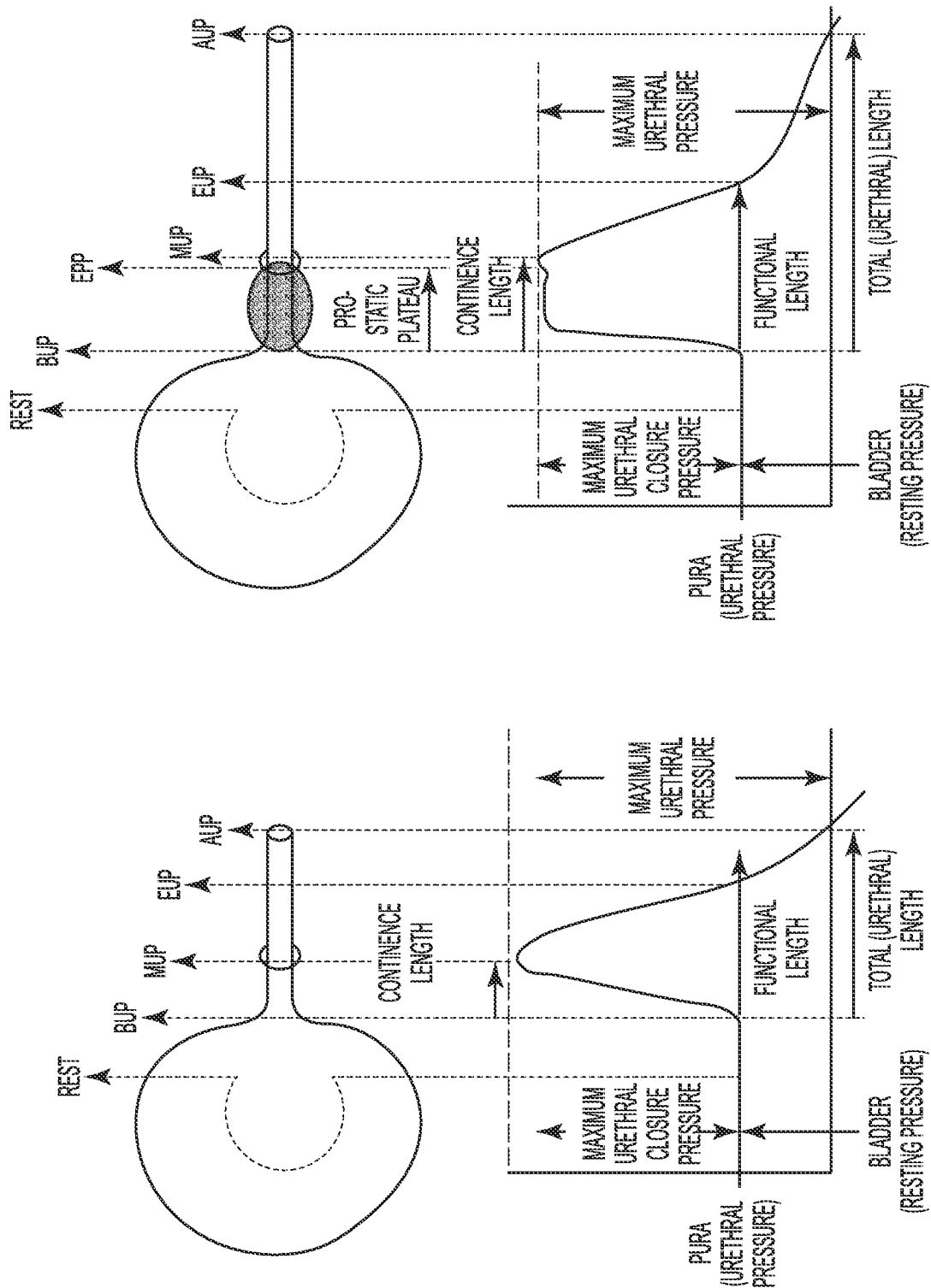
FIG. 2 is a diagram illustrating closure pressures along a urethra.

FIG. 2 is a diagram illustrating closure pressures along a urethra. Current methods for recording distributed urethral closure pressures involve a micro tip catheter with a single pressure sensor at the tip which can measure pressure in the bladder, and involve pulling the single micro tip pressure sensing catheter through the urethra in order to measure pressure at different locations in the urethra. These methods do not provide pressure distributions in the urethra in real-time. They can only measure pressure at a single point in the urethra. They also preclude the conduct of recording urethral pressure profiles during provocative maneuvers, such as coughing and val salva. Furthermore, the cost of a current single microtip pressure sensing catheter is extremely high (e.g., greater than $2000) and so even the use of these inadequate catheters poses a significant health cost. Embodiments disclosed herein using micro-sensors enable inexpensive disposable catheters that cost less than $10 each.

FIG. 3 is a diagram illustrating a pressure sensing catheter system 300 that includes a Foley catheter 302 with pressure and EMG sensors according to one embodiment. The catheter 302 includes an inflatable balloon 308 positioned near a distal end of the catheter 302. Pressure sensors 304(1)-304(9) (collectively referred to as pressure sensors 304) are formed on a sensor strip 303 and measure the contact pressure distribution in the urethra. The width available on the catheter is typically around 2 mm. Thus, the individual sensors 304 according to one embodiment are about 4×0.4 mm each or smaller. EMG electrodes 306(1) and 306(2) are formed on the sensor strip 303 proximate to pressure sensor 304(5). The sensor strip 303 is mounted at the top of the catheter 302.

In one embodiment, the sensors 304 shown in FIG. 3 are capacitive sensors for measuring pressure. The capacitance of an electrostatic capacitor is given by the following basic formula:

$$C = \frac{\varepsilon A}{d} \qquad \text{Equation I}$$

where:
C is the capacitance;
ε is dielectric permittivity;
A is the common area between two parallel plates; and
d is the distance between plates.

Figure 4A:
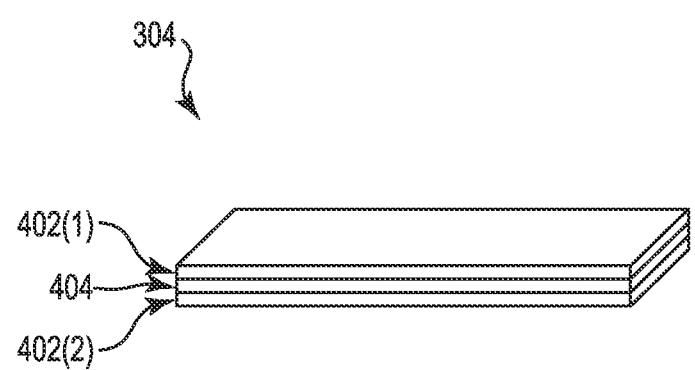
FIG. 4A is a diagram illustrating components of the capacitive sensors shown in FIG. 3 according to one embodiment.
Figure 4B:
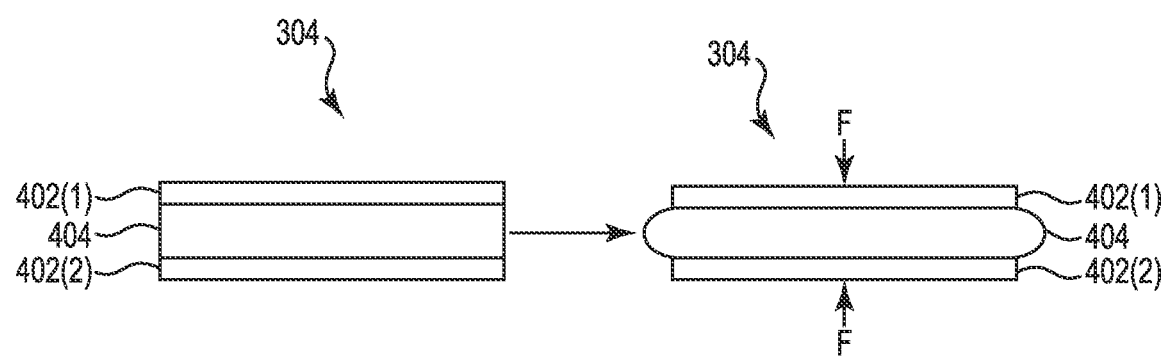
FIG. 4B is a diagram showing a compressive force being applied to a capacitive sensor and the resulting changes to the dielectric layer and the distance between the top and bottom electrodes.

In one embodiment, each of the sensors 304 shown in FIG. 3 includes two electrodes 402(1) and 402(2) (collectively referred to as electrodes 402), one electrode 402(1) on top and the other electrode 402(2) on the bottom as shown in FIG. 4A. FIG. 4A is a diagram illustrating components of the capacitive sensors 304 shown in FIG. 3 according to one embodiment. As shown in FIG. 4A, each of the capacitive sensors includes top and bottom electrodes 402 separated by a dielectric layer 404. The bottom electrode 402(2) is a sensing electrode, and the top electrode is a ground plate 402(1). The deflection of the dielectric layer 404 causes the distance between the top and bottom electrodes 402 and hence the capacitance of the sensor 304 to change. FIG. 4B is a diagram showing a compressive force, F, being applied to a capacitive sensor 304 and the resulting changes to the dielectric layer 404 and the distance between the top and bottom electrodes 402. The capacitance change can be measured and can be converted back into a pressure readout.

Figure 5:
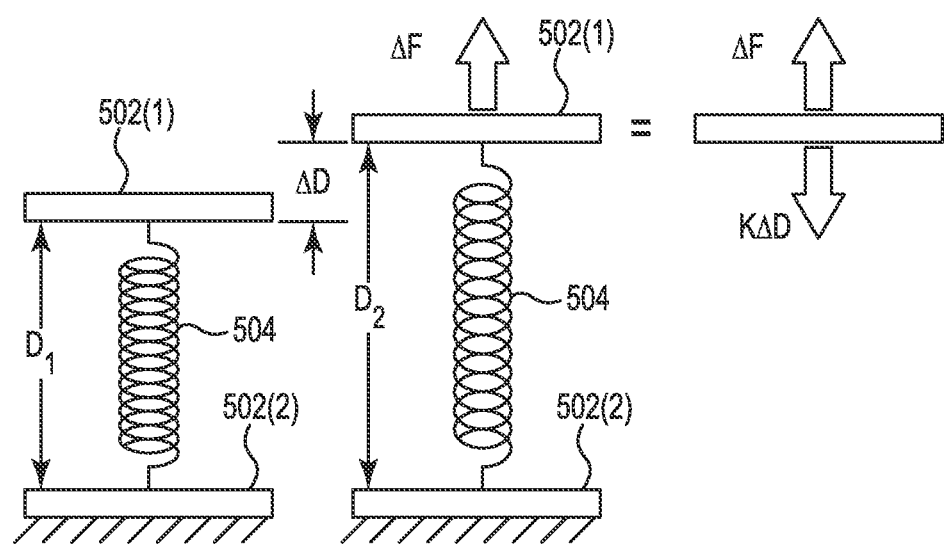
FIG. 5 is a diagram illustrating a mechanical model of a capacitor.

A capacitor can be modeled as two separate plates that are connected by a spring as shown in FIG. 5. FIG. 5 is a diagram illustrating a mechanical model of a capacitor. The dielectric layer in this model works as a spring 504. If the distance between the electrodes 502(1) and 502(2) is changed by applying a normal force to them, then the change in capacitance can be calculated as follows:

$$C = \frac{\varepsilon_0 \varepsilon_r A}{D} \qquad \text{Equation II}$$

$$dC = -\varepsilon_0 \varepsilon_r A \frac{dD}{D^2} \Rightarrow \Delta C = -\varepsilon_0 \varepsilon_r A \frac{\Delta D}{D^2} \qquad \text{Equation III}$$

$$\Delta F = k\Delta D \Rightarrow \Delta D = \frac{\Delta F}{k} \qquad \text{Equation IV}$$

$$\Delta F = A\Delta P \qquad \text{Equation V}$$

Plugging Equations IV and V into Equation III gives:

$$\Delta C = -\frac{\varepsilon_0 \varepsilon_r A^2}{D^2} \frac{\Delta P}{k} \qquad \text{Equation VI}$$

So for small changes in pressure, $\Delta C$ can be calculated using Equation VI, where C is capacitance in Farad, $\varepsilon_0$ is permittivity of air and is $8.85 \times 10^{-12}$ (F/m), $\varepsilon_r$ is permittivity of dielectric relative to air, A is the common area between two parallel plates, D is the distance between the plates, and k is the stiffness of the top electrode. An equation for the sensitivity of the sensor is given in the following Equation VII:

$$S = \frac{\Delta C}{\Delta P} \cong -\varepsilon_0 \left(\frac{\varepsilon_r}{k}\right)\left(\frac{A^2}{D^2}\right) \qquad \text{Equation VII}$$

The sensitivity depends on the stiffness of the deformable electrode. To estimate the stiffness, k, of an individual sensor, the electrode is modeled as a clamped copper rectangular membrane under uniform pressure p. The maximum deflection of rectangular diaphragms is at the center and is given in the following Equation VIII:

$$y_m = \frac{0.142pb^4}{Et^3\left(2.21\left(\frac{b}{a}\right)^3 + 1\right)} \qquad \text{Equation VIII}$$

In Equation VIII, p is the applied pressure, a is the dimension of the shorter edge, b is the dimension of the longer edge, t is the diaphragm thickness and E is the modulus of elasticity of the structural material. Since the total distance between top and bottom electrode is just 10 μm in one embodiment, while the lateral dimensions of each top electrode is 400 μm×3644 μm, it is assumed that the deformation of the membrane is linear. The approximate capacitance change due to applied pressure can then be calculated as follows.

The total capacitance after pressure is applied is the integral of the infinitesimal capacitors:

$$dC = \frac{\varepsilon l}{\cos\theta} \frac{dx}{D - \frac{2y_m}{b}x} \qquad \text{Equation IX}$$

To find the order of capacitance change, the sensor design parameters D=10 μm, $\varepsilon_r$=1, $\Delta P$=0.1 psi and $E_{copper}$=17.0× $10^6$ psi for copper electrode are plugged into Equations VIII and IX, which gives $y_m$=3 nm and $\Delta C \cong 0.5$ fF. Thus, the theoretical sensor sensitivity is expected to be 5 fF/psi. This level of capacitance change can be easily measured using commercial capacitance measurement chips.

This analysis has shown that a sensitivity capable of measuring 0.1 psi can be achieved by each of the sensors 304 in the strip 303.

Equation VII can be rewritten as:

$$S = -\varepsilon_0 \lambda \beta^2 \qquad \text{Equation X}$$

In Equation X, $\lambda$ is a material parameter that is the ratio of electrical permittivity to mechanical stiffness and $\beta$ is a geometric parameter and is the ratio of the common area of the electrodes to their relative distance. To improve sensitivity, $\lambda$ and $\beta$ are made as high as possible.

Figure 6:
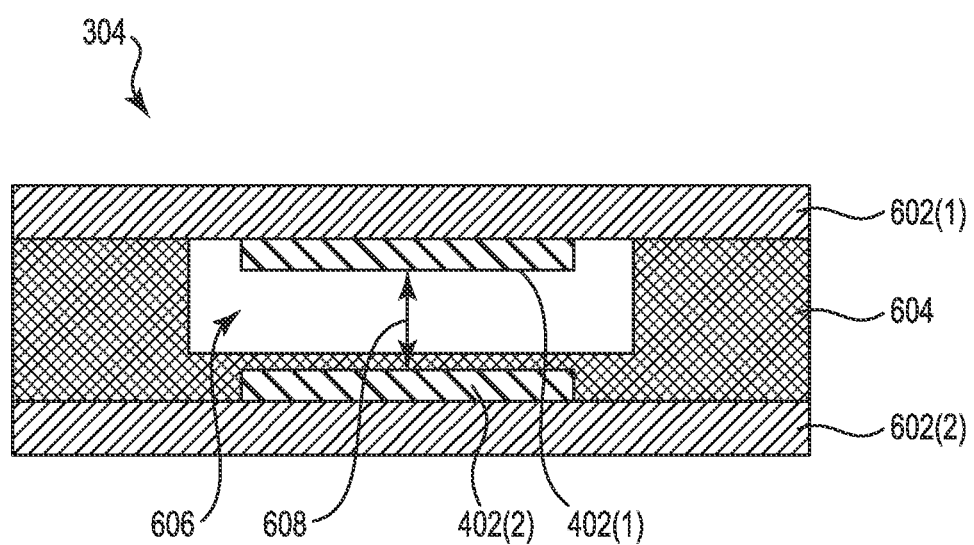
FIG. 6 is a diagram illustrating a more detailed view of components of the capacitive sensors shown in FIG. 3 according to one embodiment.

FIG. 6 is a diagram illustrating a more detailed view of components of the capacitive sensors 304 shown in FIG. 3 according to one embodiment. In the illustrated embodiment, each of the capacitive sensors 304 includes top polyimide (PI) layer 602(1) and bottom polyimide layer 602(2) (collectively referred to as polyimide layers 602); top copper electrode 402(1) and bottom copper electrode 402(2) formed on the top and bottom polyimide layers 602(1) and 602(2), respectively; a PolyDiMethylSiloxane (PDMS) spacer layer 604 separating the top and bottom polyimide layers 602(1) and 602(2); and a dielectric layer 606. The bottom copper electrode 402(2) according to one embodiment senses the capacitance that is related to applied pressure. The height of the electrodeposited (ED) bottom copper electrode layer 402(2) on the bottom polyimide layer 602(2) is 12 μm in one embodiment. The dielectric layer 606 according to one embodiment is an air cavity in a PDMS frame that minimizes resistance to deformation of the top electrode 402(1) and allows a large deformation of the top electrode 402(1). The distance 608 between the top and bottom electrodes according to one embodiment is 10 μm. The top deformable common electrode 402(1), which is an electrodeposited copper layer on the top polyimide layer 602(1), is also a ground plate. The height of the electrodeposited top copper electrode layer 402(1) on the top polyimide layer 602(1) is 12 μm in one embodiment.

FIGS. 7A-7F are diagrams illustrating a process for forming the capacitive sensors 304 shown in FIG. 3 according to one embodiment. As shown in FIG. 7A, the fabrication process starts with a Poly Ethylene Terephthalate (PET) layer 702 (Grafix Clear 0.005 Dura-Lar Film) as the substrate. PET is the transparency used in laser printers and is flexible and transparent. This helps in cutting out the sensor and at the same time provides optical transparency which is important later in the alignment of the top and bottom electrodes during assembly. The sensors and signal lines are made on polyimide layer 706, which in one embodiment is AC091200EV (from DuPont Flexible Circuit Materials Group) which is a polyimide sheet with a 9 μm electrode-posited copper layer 708.

To add polyimide layer 706 to PET layer 702 as the substrate, lift-off-resist 10 μm LOR 20B layer 704 (Micro-Chem Corporation) is coated (spun) on the PET layer 702, as shown in FIG. 7B. The LOR layer 704 is a sacrificial layer that is dissolved in developer to release the sensor at the end of the fabrication process. Then the polyimide layer 706 is added on the top of the LOR layer 704, as shown in FIG. 7C. Then the setup is put on hotplate at 65° C. for 10 minutes to cure the LOR layer 704. Then patterning the copper layer 708 to create the electrodes is initiated by coating the copper layer 708 by 2 μm photoresist 1813 (MicroChem Corporation) layer 710, as shown in FIG. 7D, followed by a photolithography step as shown in FIG. 7E. Because the thermal expansion coefficient is higher for the copper layer 708 than the polyimide layer 706 and the PET layer 702, the setup cannot withstand temperature higher than 70° C. Otherwise the copper layer 708 will expand more than the polymer layers and everything will irreversibly deform. So the standard operating procedure for curing the photoresist layer 710 was changed to be soft baked at 65° C. for 3 minutes and hard baked at 65° C. for 15 minutes after photolithography. The electrodes and traces are then made, as shown in FIG. 7F, by submerging it into copper etchant $FeCl_3:H_2O$ 1:8 (v/v) (MG Chemicals 415 Ferric Chloride Liquid), at 50° C. in the solution for 40 minutes. The copper etch rate is about 225 nm/min in this solution. Subsequently, the photoresist layer 710 is washed out in acetone and the electrodes are checked under a microscope and tested with a multi-meter to ensure the integrity of all signal lines and electrodes. The resulting structure comprises fabricated electrodes on a translucent and flexible polymer substrate polyimide. The bottom electrodes have respective signal trace lines that carry the voltage signals along the sensor strip to the proximal end of the catheter, and separate trace lines for the top electrodes are also included on the sensor strip.

Figure 8A:
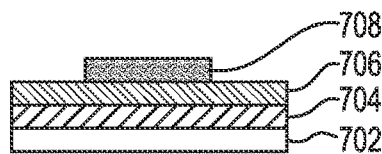
FIGS. 8A-8F are diagrams illustrating additional steps of a process for forming the capacitive sensors shown in FIG. 3 according to one embodiment.

After fabrication of the top and bottom copper electrodes as described above, a spacer layer from PDMS (Sylgard 184, Dow Corning) is added to hold the structure of the sensor together. PDMS is utilized for this purpose because it is transparent and flexible, which makes it useful for this application. FIGS. 8A-8F are diagrams illustrating additional steps of a process for forming the capacitive sensors 304 shown in FIG. 3 according to one embodiment. FIG. 8A shows the structure after completing the steps described above with reference to FIGS. 7A-7F. The illustrated structure includes a PET layer 702, a LOR layer 704 formed on the PET layer 702, a polyimide layer 706 formed on the LOR layer 704, and a copper (electrode) layer 708 formed on the polyimide layer 706. The next step is to add a spacer layer 802.

Figure 8B:
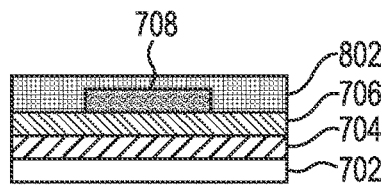

For the spacer layer 802, PDMS is spun on both top and bottom electrodes separately. FIG. 8B shows the structure after a PDMS spacer layer 802 has been applied. The thickness of the PDMS spacer layer 802 on the bottom electrode is 5 μm in one embodiment. The PDMS spacer layer 802 helps prevent any short circuits between the top and bottom electrodes in the case of exceeding the designed pressure range. The thickness of the PDMS spacer layer 802 on the top electrode is 5 μm for making the air cavity layer to allow deformation between the top and bottom electrodes. To make the cavity, the PDMS spacer layer 802 is etched in an STS etch machine. After coating the electrodes with the PDMS spacer layer 802, they are placed on a hotplate at 65° C. for 3 hours for curing.

Figure 8C:
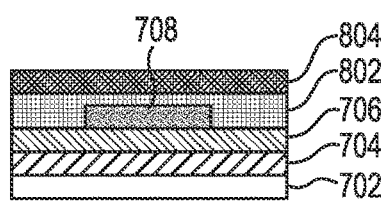
Figure 8D:
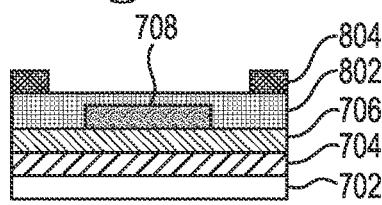
Figure 8E:
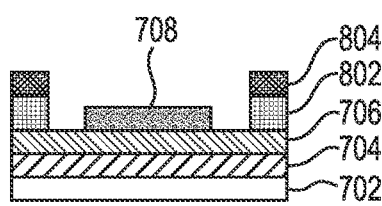

To make the air cavity, the PDMS layer 802 in the top electrode is etched. For this purpose, photoresist layer 804 (AZ9260) is spun, baked and patterned on the PDMS layer 802 to make a masking layer, as shown in FIGS. 8C and 8D. The thickness of the photoresist layer 804 is 20 μm in one embodiment. The structure is then soft baked at 70° C. for 3 minutes with no hard bake. To make the 5 μm cavity, the PDMS layer 802 on the top electrode is fully etched by plasma in an STS etch machine ($SF_6$, 45 sccm, $O_2$, 15 sccm, 100 mTorr, 100 W). The resulting structure is shown in FIG. 8E. The etching rate in one embodiment is 150 nm/min. After checking the etched profile with a surface profiler, the top and bottom electrodes on PET for each sensor are cut out by scissors. They are put in oxygen plasma ($O_2$:75 sccm, 100 W) to clean the PDMS surface and prepare them for bonding. Alignment between top and bottom electrode-PDMS assemblies is done within 10 minutes, otherwise the surface may need to be treated by oxygen plasma again.

Figure 8F:
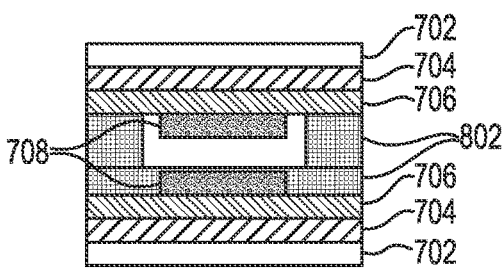

FIG. 8F shows the alignment of the top and bottom electrode structures, and the PDMS to PDMS bonding of these two structures. A four degree of freedom aligner is used for the aligning step. Since the electrodes are flexible, they may easily wrinkle and create small waves on top of the substrate. Wrinkles can produce variability in the sensor resolution and range. The aligner holds the top and bottom electrodes by vacuum. The bottom stage can move in x and y directions and rotate around the z-axis while the top electrode moves just in the z direction. Backlight is provided by LEDs to see through the sensor. This is because of the polyimide layer 706 being translucent. Alignment marks are visible if there is enough light from the bottom of the aligner. After turning on the LEDs, alignment marks can be seen. After lining up of the alignment marks and pressing the top and bottom layers slightly together, the vacuum is released. Then the whole setup is placed between two glassware slides and put on a hotplate at 70° C. for 10 hours. Two 100 g calibrating weights are put on the glassware slide to provide uniform pressure for the PDMS to PDMS bonding. Finally, to release the sensor, it is put in $AZ400K:H_2O$ 1:5 (v/v) for 3 hours with 40% ultrasound. AZ400K dissolves LOR layers 704 and releases the sensor from PET layers 702.

Figure 9:
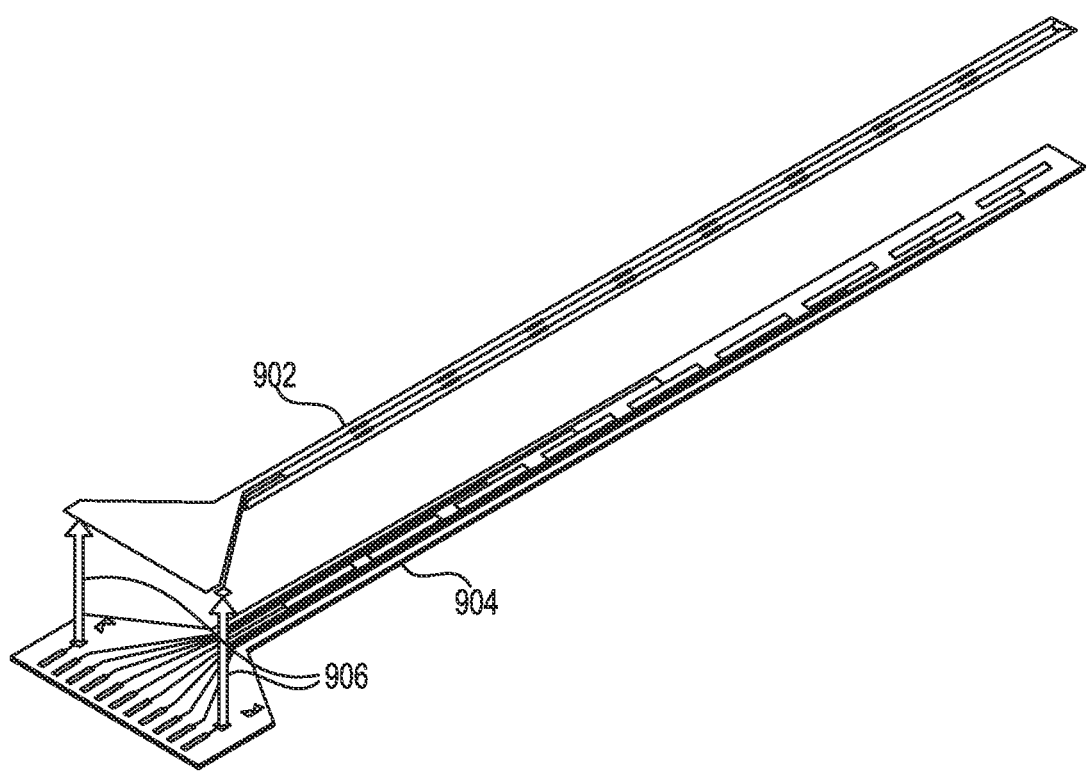
FIG. 9 is a diagram illustrating the alignment of the top electrode structure and the bottom electrode structure according to one embodiment.

FIG. 9 is a diagram illustrating the alignment of the top electrode structure 902 and the bottom electrode structure 904 according to one embodiment. The top common ground electrode structure 902 makes contact with a ground trace line on the bottom substrate 904 through conductive silver epoxy 906 after the PDMS-top-electrode structure 902 is flip-chip assembled on the sensor strip.

Figure 10:
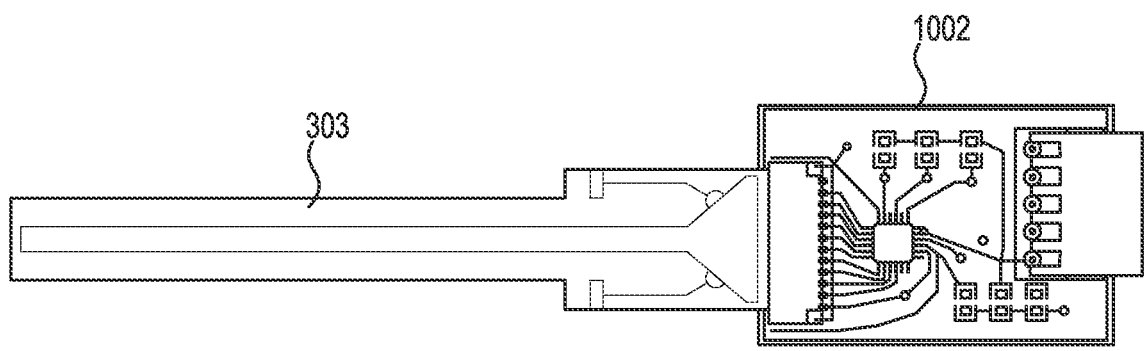
FIG. 10 is a diagram showing the sensor array connected to a printed circuit board (PCB).

After alignment and bonding are completed, the sensor is cut out of the polyimide to be sandwiched between external PDMS layers for protection from liquid. Then the sensor is connected to a data acquisition device on a printed circuit board (PCB). FIG. 10 is a diagram showing the sensor strip or sensor array 303 connected to the PCB 1002. The connections between the sensor array 303 and the PCB 1002 are made in one embodiment by a zero-insertion-force connector for flexible circuits. In one embodiment, the data acquisition module includes a 16-bit capacitance to digital converter (CDC) chip, AD7147 (AnalogDevice) that reads the capacitance in the range of ±8 pF with ¼ of femto Farad resolution.

In one embodiment, a 7 Fr. (2.3 mm diameter) Foley catheter is used as the device to be instrumented by the sensor array 303. In another embodiment, an 8 Fr. (2.6 mm diameter) Foley catheter is used as the device to be instrumented by the sensor array 303. The catheter has three separate lumens from the beginning all the way down the length of the catheter to the ending point inside the bladder: one square shape Lumen (1100×1100 µm$^2$) that is open at both ends, and allows urine to drain out into a collection bag; and two small and circular lumens (diameter 100 µm) that connect to a balloon at the tip. The balloon is inflated with air when it is inside the bladder to prevent the catheter from coming out of the bladder.

Figure 11:
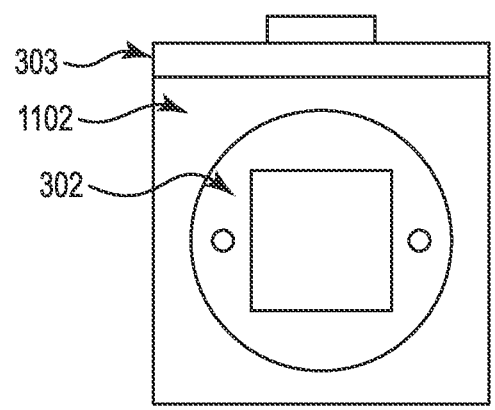
FIG. 11 is a diagram illustrating the sensor array coupled to a catheter according to one embodiment.

FIG. 11 is a diagram illustrating the sensor array 303 coupled to a catheter 302 according to one embodiment. To install the sensor array 303 on the catheter 302, a rectangular PDMS block 1102 (transparent and flexible) is fabricated around the catheter 302 by molding. PDMS is used to stick the micro-fabricated sensor array 303 to the flat surface. The sensors 304 (FIG. 3) of the sensor array 303 make contact with the sphincter muscles inside the urethra to measure the urethral pressure profile. The signals are sent out on the catheter through traces in the sensor array 303 to the capacitance to digital converter chip on the PCB 1002 (FIG. 10). The PCB 1002 sends the data to a computer for analysis. In one embodiment, the PCB 1002 is fully covered by a layer of hot melt adhesive (HMA) so as to protect all the electronics on it from liquid/urine.

The interface between the PI and PDMS layers does not get damaged by bending or by contact with liquid. The sensing strip 303 has been immersed in saline for several hours to test the strength of the PI-PDMS adhesion. It was found that the layers do not delaminate even after several hours of immersion in saline. It should be noted that the sensor strip 303 according to one embodiment is disposable for one-time use.

An in-vitro evaluation of a sensor array 303 constructed as described herein has been performed. The sensor array 303 was tested in an air pressure chamber in which the internal pressure could be controlled to different static values in the range of 0-5 psi with 0.1 psi resolution. To do the tests, the pressure was increased from 0 to 1.0 psi in steps of 0.1 psi. Also a reference pressure sensor MS5534C manufactured by Intersema was placed inside the chamber for calibration purpose (resolution 0.15 psi).

Figure 12:
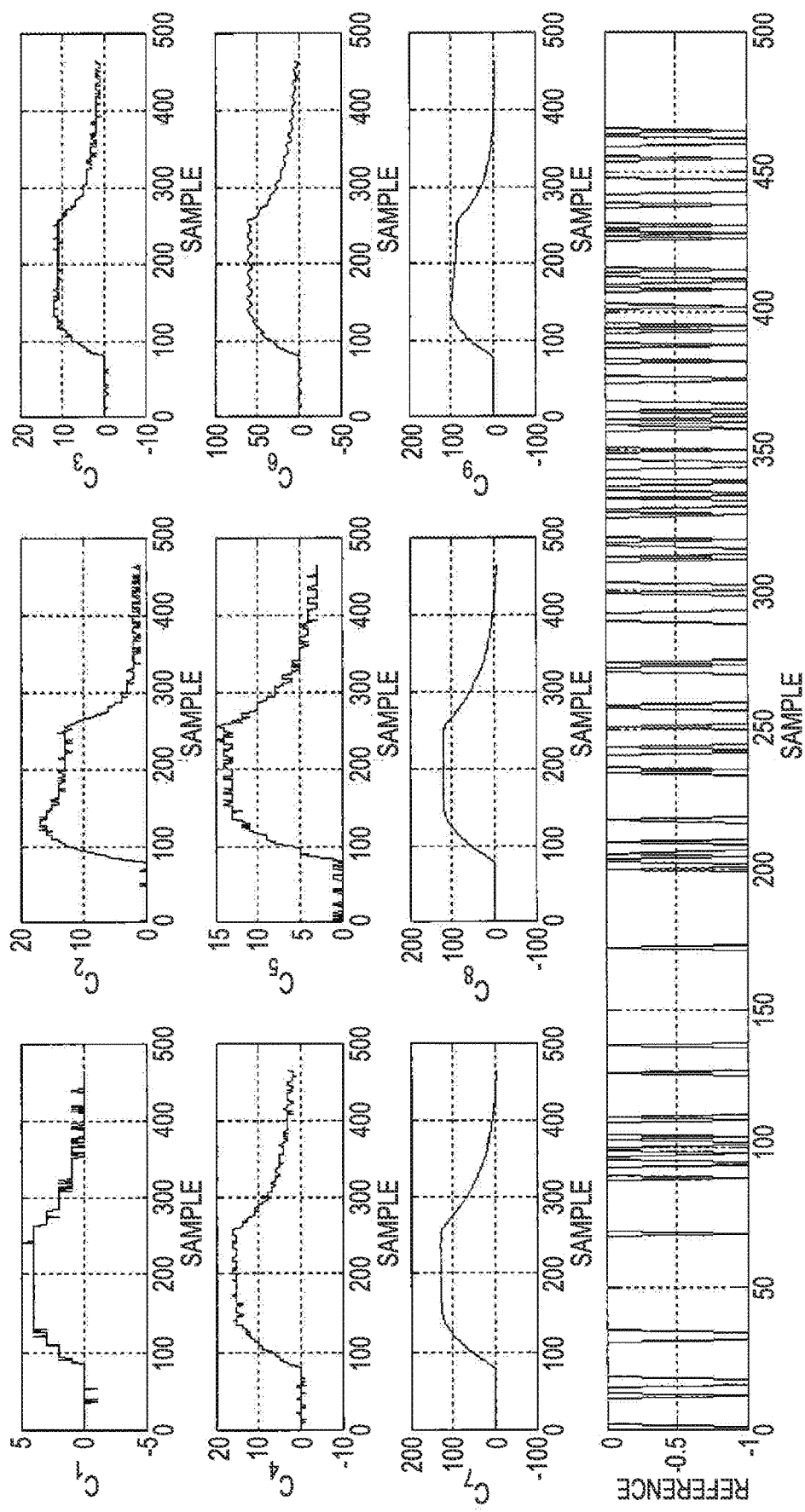
FIGS. 12-15 shows results of tests on the sensor array.

FIGS. 12-15 shows results of the tests on the sensor array. FIG. 12 shows the sensor responses for a pressure of 0.1 psi. As shown in this Figure, all of the sensors respond with an adequate sensitivity to the 0.1 psi pressure change. In this Figure, the capacitance change is shown on the vertical axis. The responses of the sensors are not equal. This variability in sensitivity is suspected to be due to unequal gaps obtained from the sensor assembly. Nonetheless, even the least sensitive sensor resolution is better than 0.1 psi. The difference in sensitivities can be eliminated by calibrating, so that all sensors provide readings in psi after calibration. The sampling time used is 170 milli-seconds.

Figure 13:
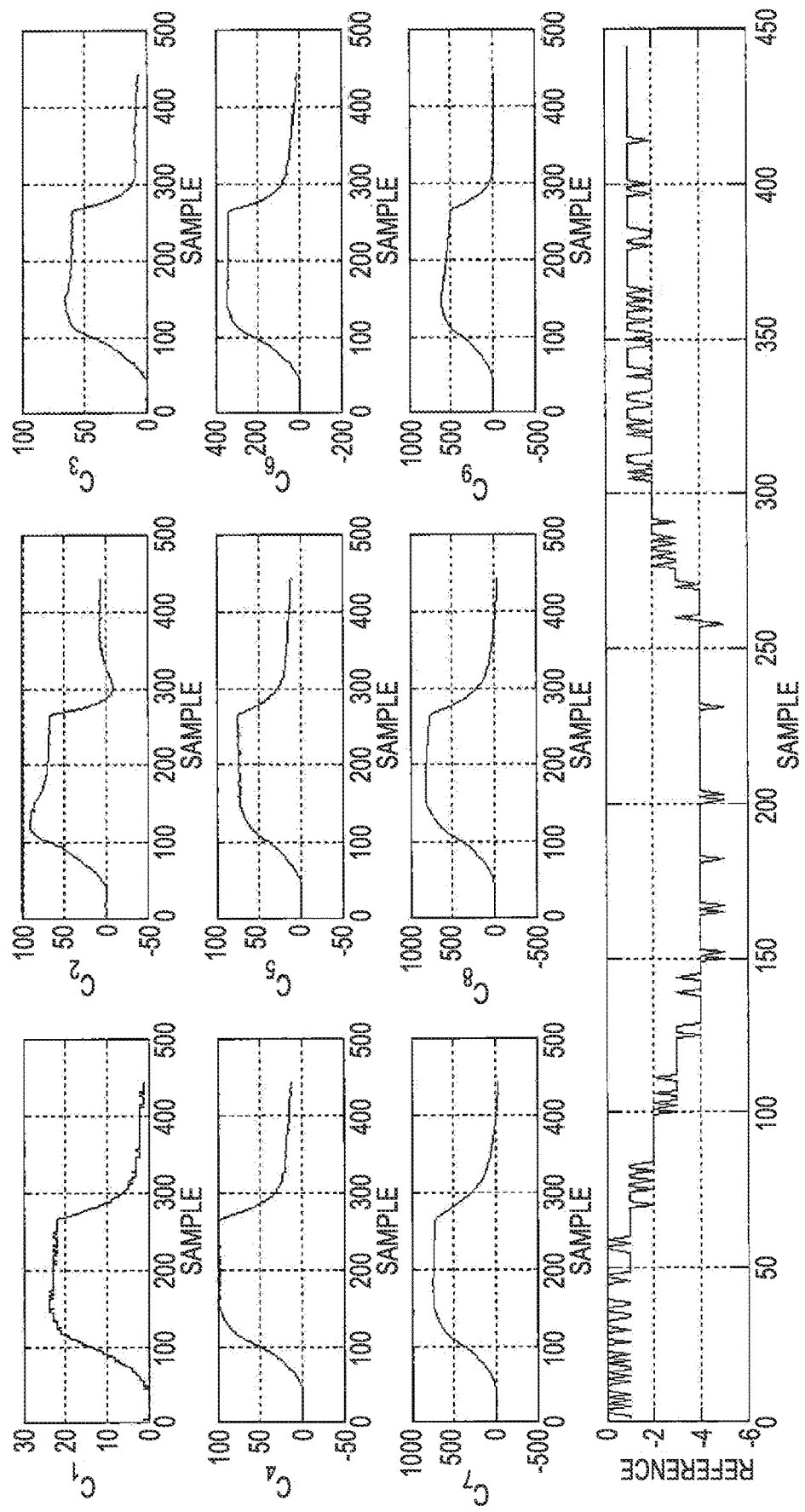
Figure 14:
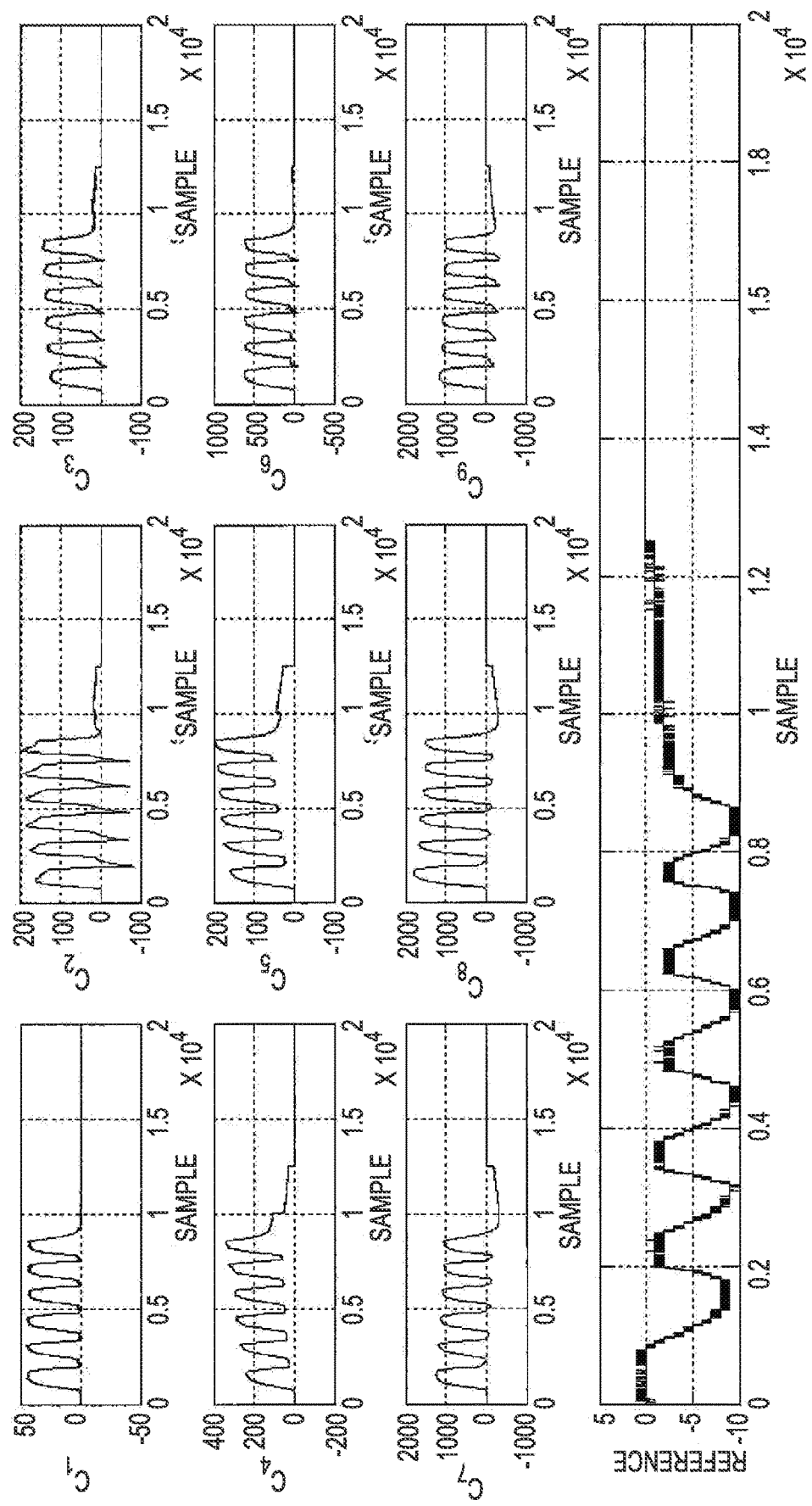
Figure 15:
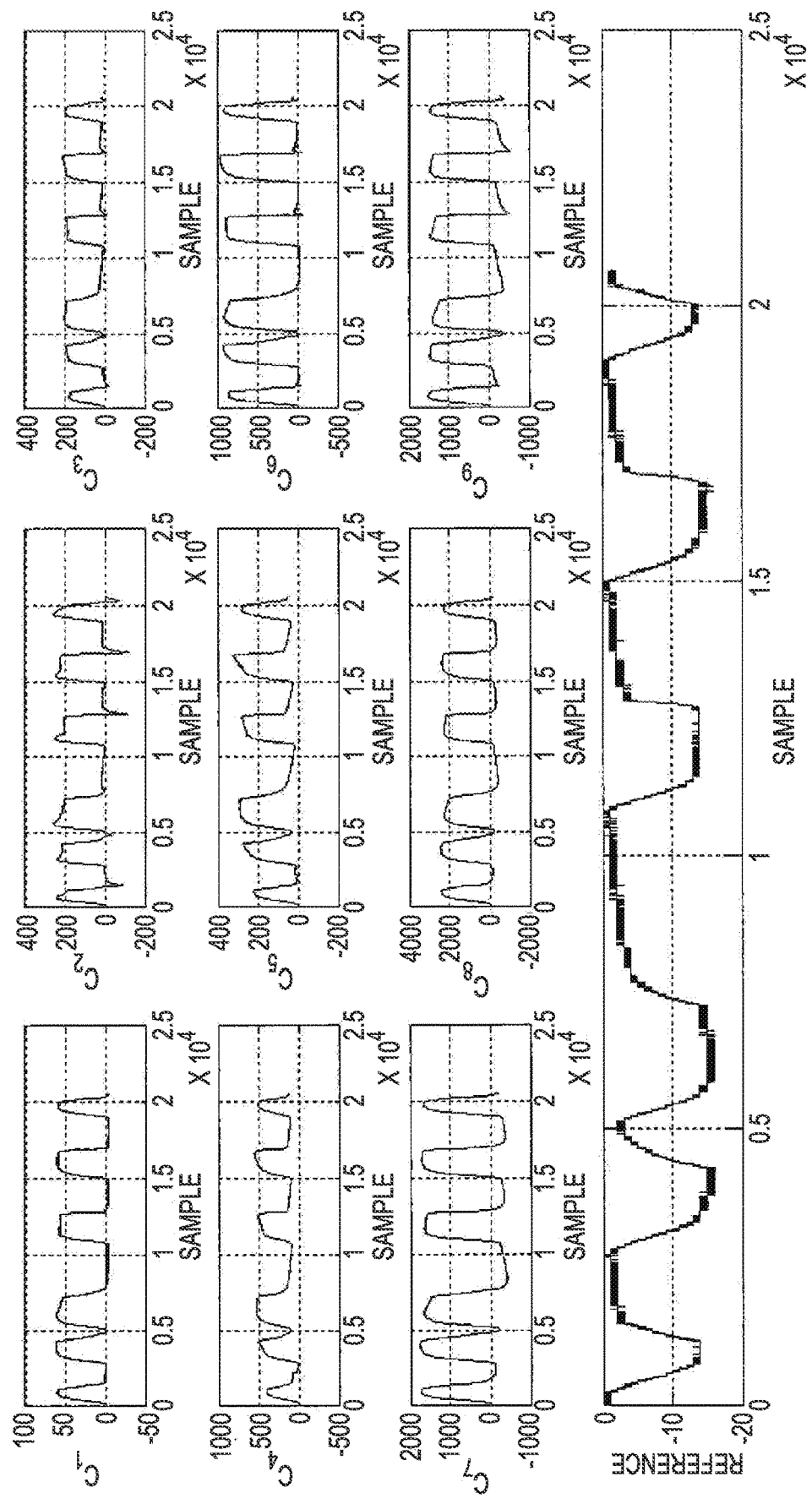

FIG. 13 shows the sensor responses for a pressure of 1.0 psi. It can be seen that the reference sensor (which is provided to measure parasitic capacitance) does not respond to changes in air pressure in the chamber. Thus, readings from the reference sensor can be used to compensate for parasitic capacitance changes that occur due to closeness to the human body. FIG. 14 shows the sensor responses for a pressure of 2.0 psi. FIG. 15 shows the sensor responses for a pressure of 3.0 psi. The capacitance change is shown along the vertical axis. The order of the sensors C1-C9 corresponds to the order shown in FIG. 3.

Proximity to a human body can introduce significant parasitic capacitance into the sensor array 303. The human body surface acts like the top electrode of a capacitor that is connected to a virtual ground. This capacitance is very low and in order of pF, but it is of the same order as the strength of the capacitance signal due to applied pressure in embodiments of this disclosure. When applied pressure is small, the deflection in the capacitors is small and so is the change in capacitance. This capacitance change due to applied pressure, in the range of 0.1-0.2 psi, is in the magnitude of the parasitic capacitance produced by the human body. Therefore, signal processing techniques are utilized to remove parasitic effects. For this purpose, a single free bottom electrode (without the corresponding top electrode) is fabricated on the sensing strip 303 to measure the parasitic capacitance without being sensitive to pressure.

The signals from the pressure sensors are given by:

$$\begin{bmatrix} S_1 \\ \vdots \\ S_9 \end{bmatrix} = \begin{bmatrix} F_1 \\ \vdots \\ F_9 \end{bmatrix} + \begin{bmatrix} a_1 & & 0 \\ & \ddots & \\ 0 & & a_9 \end{bmatrix} \begin{bmatrix} R_1 \\ \vdots \\ R_9 \end{bmatrix} \qquad \text{Equation XI}$$

where:

vector S is the signal that contains both parasitic and pressure signals;

F is a vector that is the created signal by applied pressure;

R is the parasitic signal that is captured by the reference electrode; and a is the coefficient matrix that relates the parasitic signal to the sensors.

Figure 16:
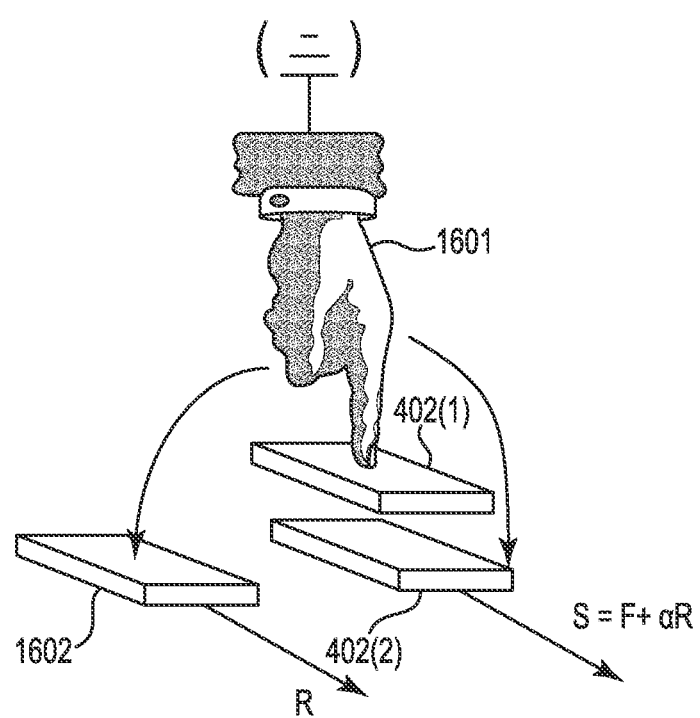
FIG. 16 is a diagram illustrating parasitic capacitance on the sensor array created by a human hand.
Figure 17:
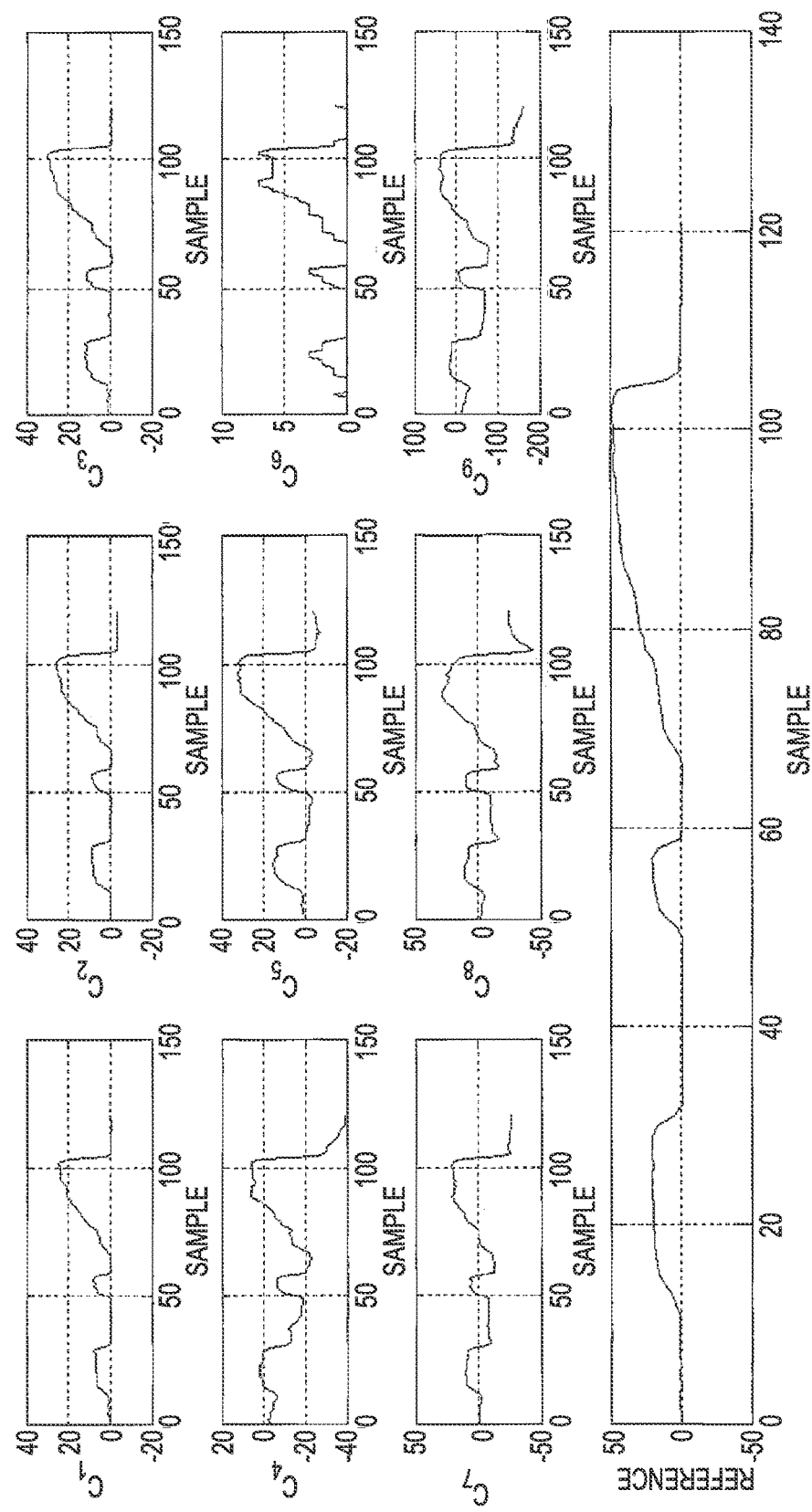
FIG. 17 shows the results on the array when a human hand comes close to the sensor array while there is no pressure applied.

FIG. 16 is a diagram illustrating parasitic capacitance on the sensor array 303 created by a human hand 1601. The "R" in FIG. 16 is the reference signal from the reference electrode 1602 that captures the parasitic electrical field. FIG. 17 shows the results on the array when a human hand comes close to the sensor array 303 while there is no pressure applied. Parasitic capacitance can be seen on all the channels. The reference signal, R, is used to remove the noise and clean the signals. The a coefficients in Equation XI can be found here because the vector F is zero. It is assumed that when the sensor array is inserted into the human body, all the sensors are covered uniformly with the tissue, so the coefficient matrix [$a_{ij}$] is constant. With this assumption, the coefficient matrix [$a_{ij}$] can be found by setting pressure to be zero (F=0) and only measuring the influence of the human tissue.

The effect of adding more tissue on the parasitic capacitance when a sensor 304 is already covered by tissue has been evaluated. When all the sensors 304 are covered uniformly with tissue, bringing more tissue close to the sensor 304 does not change the capacitance significantly. In this test, at first the sensors 304 were covered by one hand when another hand comes close and covers over the first hand. A significant change is not seen in the sensors 304.

Based on the parasitic data that is determined by measuring only the influence of the human tissue, the coefficient matrix [$a_{ij}$] is calculated. Pressure and parasitic capacitance are the applied at the same time. Pressure inside the chamber is increased while a human hand is simultaneously moved closer and further from the setup. The previously calculated calibration coefficients [$a_{ij}$] are used to remove the influence of the parasitic capacitance R so that only the response due to pressure is obtained.

Figure 18:
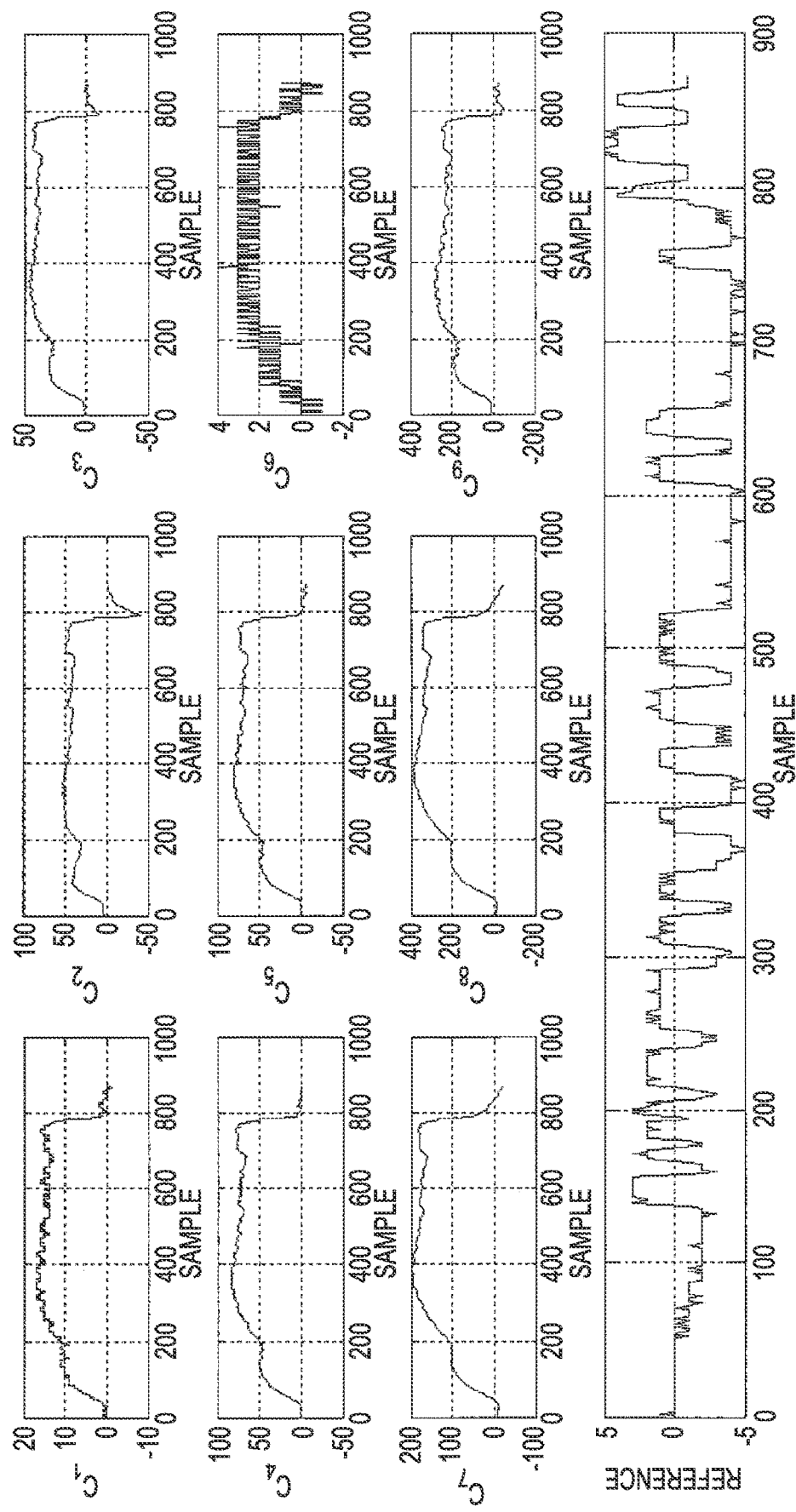
FIG. 18 shows test results for the sensor array when a 0.5 psi pressure was applied to the array and at the same time a user's hand got close and far from the sensor for multiple times.

In one embodiment, the elements of the matrix [$a_{ij}$] may be updated by an adaptive law during the measurement. After finding the values of the elements of the coefficient matrix, they can be used in tests where a pressure signal is also present. The condition in the two experiments should be the same otherwise the matrix [$a_{ij}$] may be updated by an adaptive law. FIG. 18 shows test results for the sensor array when a 0.5 psi pressure was applied to the array and at the same time a user's hand got close and far from the sensor for multiple times.

Figure 19:
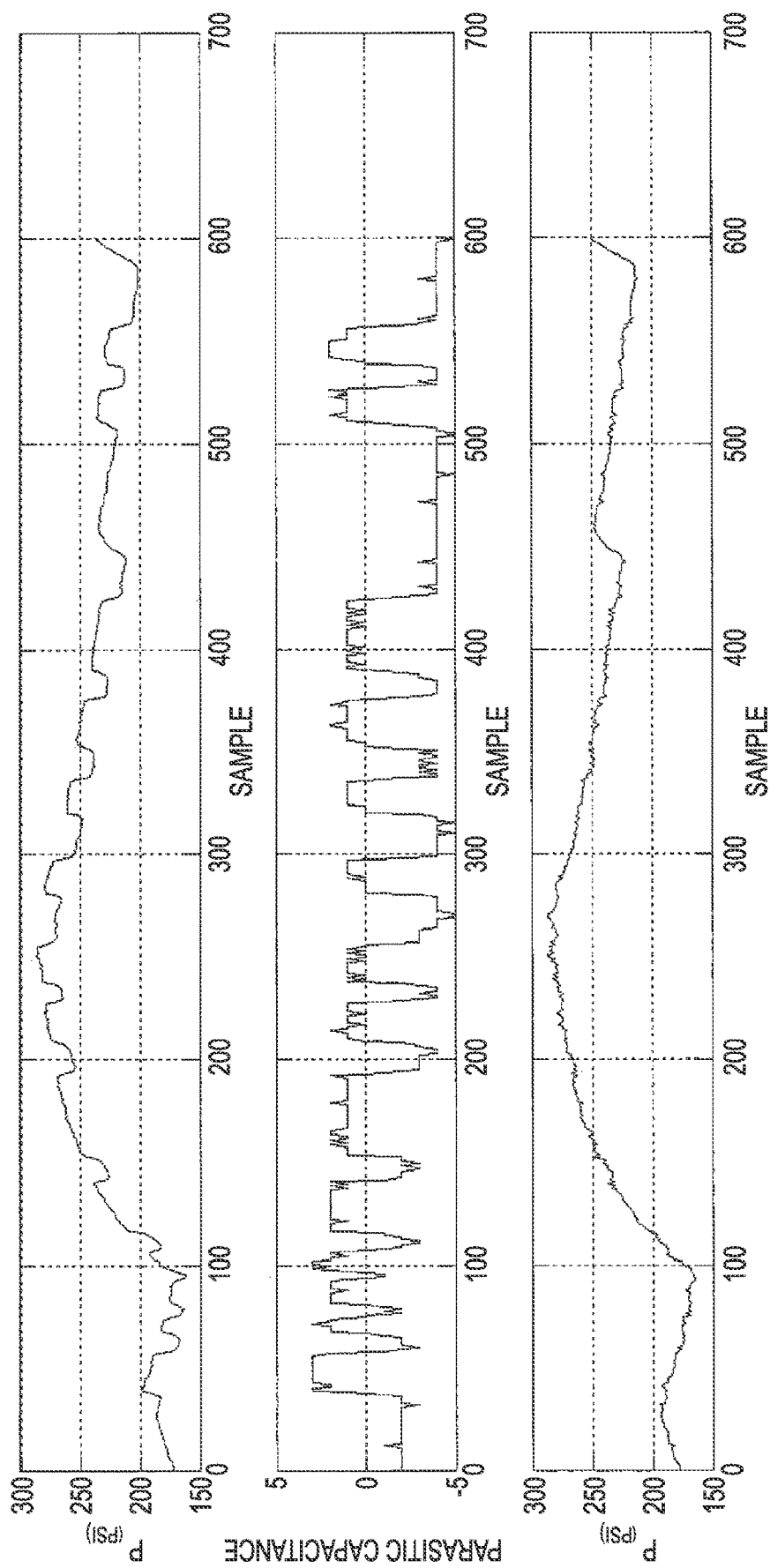
FIG. 19 shows test results for the sensor array, including a noisy sensor signal (top graph), noise from the reference (middle graph), and a cleaned signal (bottom graph).

Using the calculated a matrix and the reference, the signal in sensor number 9 is cleaned, and the results are shown in FIG. 19. FIG. 19 shows test results for the sensor array, including a noisy sensor signal (top graph), noise from the reference (middle graph), and a cleaned signal (bottom graph).

FIG. 20A is a diagram illustrating signal lines (traces) of the sensor array 303 according to one embodiment. FIG. 20B is a diagram illustrating an expanded view of a proximal portion of the sensor array 303 shown in FIG. 20A. The left side of the sensor array shown in FIG. 20A includes 14 signal lines 2002(1)-2002(14) collectively referred to as signal lines 2002. Going from top to bottom: The top or first signal line 2002(1) is connected to ground; the next signal line 2002(2) is connected to the reference electrode 1602 (FIG. 16) for measurement of parasitic capacitance caused by closeness to a human body; the next nine signal lines 2002(3)-2002(11) are each connected to a respective one of the nine pressure sensors 304(1)-304(9); the next signal line 2002(12) is an ACS line; and the last two signal lines 2002(13) and 2002(14) are piezoresistive transducer lines for measurement of capacitance due to bending of the sensor array.

Figure 21:
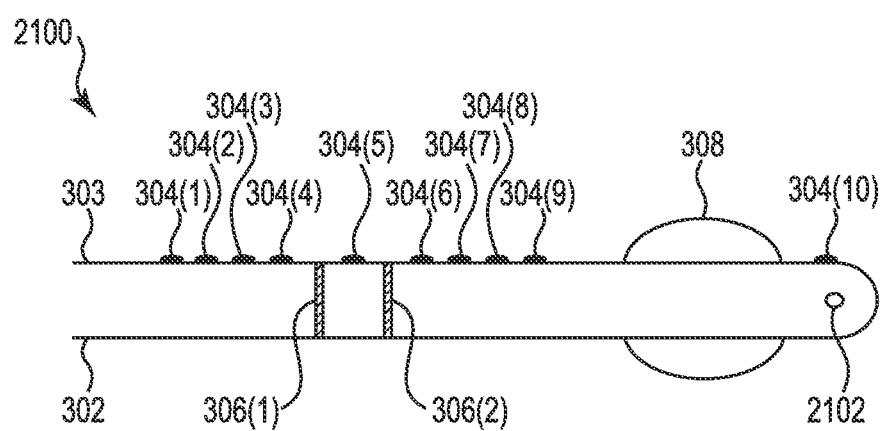
FIG. 21 is a diagram illustrating a pressure sensing catheter system that includes a Foley catheter with pressure and EMG sensors according to another embodiment.

FIG. 21 is a diagram illustrating a pressure sensing catheter system 2100 that includes a Foley catheter 302 with pressure and EMG sensors according to another embodiment. The catheter 302 includes pressure sensors 304(1)-304(10) (collectively referred to as pressure sensors 304), and two ring EMG electrodes 306(1) and 306(2) (collectively referred to as EMG electrodes 306). In one embodiment, the pressure sensors 304 are implemented in a sensor strip 303 that slides into a slot in the catheter 302. The catheter 302 includes a retention balloon 308 to help the catheter 302 stay inside the urethra, and a bladder opening 2102 for filling and voiding. Pressure sensors 304(1)-304(9) measure the contact pressure distribution in the urethra. Since the urethra length is about 4 cm in humans, the nine pressure sensors 304(1)-304(9) are each separated by a distance of about 5 mm, and are all located within 4 cm in one embodiment. To use the maximum available space on the catheter 302, the width of each capacitive sensor on the strip 303 is chosen in one embodiment to be 400 μm and the length to be 3.64 mm in order to accommodate nine sensors 304 in the urethra. The typical maximum pressure inside the bladder that needs to be measured is about 100 cmH$_2$O which is 1.42 psi. The specifications according to one embodiment were therefore chosen as a sensing resolution of 0.1 psi with a maximum pressure reading capability of 5 psi.

Figure 22:
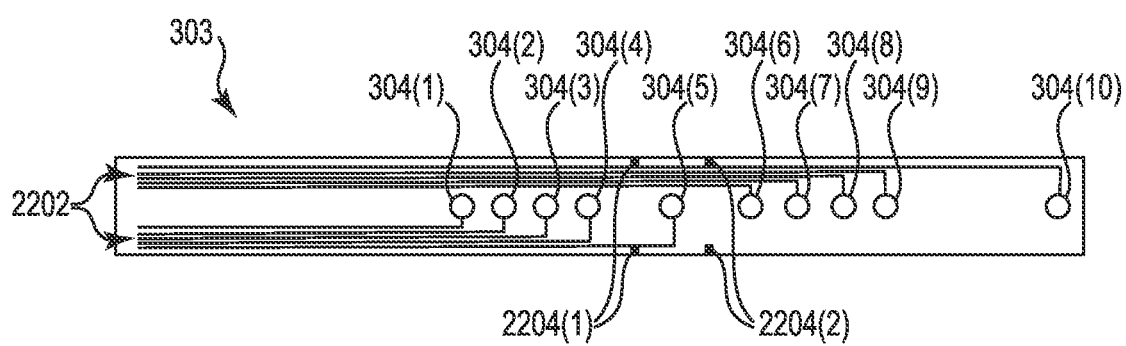
FIG. 22 is a diagram illustrating a sensor strip that includes pressure sensors and two sets of slots for EMG electrodes.

FIG. 22 is a diagram illustrating a sensor strip 303 that includes pressure sensors 304(1)-304(10) (collectively referred to as pressure sensors 304) and two sets of slots 2204(1) and 2204(2) for EMG electrodes. The sensor strip 303 includes electrical signal lines 2202 coupled to the pressure sensors, which are covered with insulation (not shown). The sensor strip 303 is configured to slide into a slot made at the top of a urethral catheter.

Figure 23:
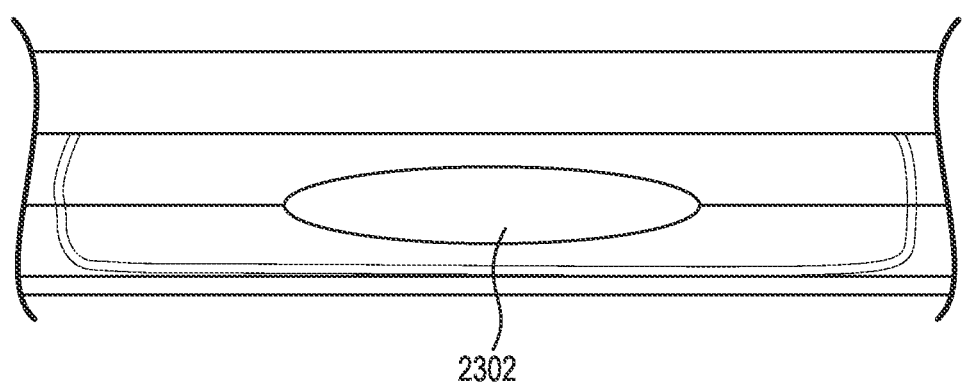
FIG. 23 shows an elliptical electrode of a pressure sensor according to one embodiment.

In one embodiment, the pressure sensors of the sensor strip 303 include electrodes having an elliptical shape. FIG. 23 shows an elliptical electrode 2302 of a pressure sensor 304 according to one embodiment. The elliptical electrodes inscribed on a rectangular substrate help reduce the stiffness of the deflecting diaphragm of the pressure sensor, and increases displacement. In another embodiment, the electrodes have a rectangular shape equal in size to that of the substrate. In yet another embodiment, the electrodes have a spring shape.

The instrumented urethral catheter disclosed herein is capable of simultaneously measuring pressure distribution in the urethra and neural signals from the urethral sphincter. This catheter can provide significantly improved urodynamic diagnosis for addressing urinary incontinence, help determine structural and neurological causes of urinary incontinence, provide instantaneous and continuous measurements of functional urethral length, and help in determining appropriate rational procedures for surgical intervention. The catheter enables useful urethral pressure measurements during provocative actions such as coughing and val salva maneuvers.

Features of the instrumented urethral catheter with a capability to measure pressure and forces at multiple locations in the urethra include: (1) It can provide simultaneous measurement of pressure at multiple locations in the urethra with one static device, instead of the current technique of moving the device to measure pressure at one location at a time; (2) it can provide real-time measurement of the distribution of pressure and can be used for urethral measurement during provocative maneuvers, such as coughing, pressing the stomach, etc.; (3) it can make sphincter EMG measurements at the same time, so as to enable time correlation between neural signals and urethral pressure distribution profiles; (4) the sensing device is highly flexible for insertion into the urethra and highly compact for inclusion on a 2.6 mm diameter catheter; (5) the sensor system relies on an inexpensive disposable sensor strip that can be utilized with catheters of various sizes; (6) pressure measurement artifacts due to bending of the sensing strip are automatically compensated for; (7) parasitic readings due to human body proximity changes are automatically compensated for; and (8) the sensors contain features to facilitate measuring low values of urethral pressure, such as elliptical electrodes, small gaps and thin sensing diaphragms.

As described above, microfabrication techniques have been used to develop an instrumented catheter with a capability to robustly measure pressure and forces at multiple locations and simultaneously measure muscle EMG signals. The instrumented catheter provides simultaneous measurement of pressure at multiple locations in the urethra with one static device, instead of the existing technique of moving the device to measure pressure at different urethral locations. Embodiments disclosed herein provide real-time measurement of the distribution of pressure and can be used for measurement during provocative maneuvers. The sensor strip is provided with EMG sensors, in addition to pressure measurement sensors. Measurement of distributed urethral pressures and EMG simultaneously help to distinguish between structural and neural causes of incontinence in a patient.

The sensor according to one embodiment uses pre-fabricated flexible copper-on-PI substrate. The top and bottom electrodes are fabricated separately and then assembled together using a channeled-PDMS dielectric. A custom-designed aligner to render the sensor layers to be optically transparent and enable alignment of the layers for assembly is used.

Embodiments of the device rely on an inexpensive disposable sensor strip. The sensor strip can be utilized with catheters of various sizes, as long as the slot size is standardized for the strip in all catheters. In order to obtain adequate sensitivity for measurement of low urethral pressures, capacitive sensors with small micron-sized air-gaps on a flexible substrate are used. With capacitive sensors, parasitic fringe capacitance from human tissues is a significant source of error. This error is removed by using a reference sensor that is insensitive to pressure but measures parasitic capacitance. The device utilizes signal lines embedded on the sensor strip. A single electronic interface at the distal end of the catheter enables all sensor signals to be read simultaneously. The flexibility of the sensor strip allows it to be mounted on a catheter that could undergo significant bending during insertion through the urethra. The flexibility of the sensor strip allows it to bend without destruction of the sensors or signal lines on the device. Bending of the sensing strip can cause changes in measured pressure values. To compensate for errors caused by bending, the sensing strip incorporates at least one piezoresistive transducer line that measures bending in the strip but is not sensitive to pressure on the strip. The use of this bending measurement line enables compensation for bending errors.

Closeness to the human body, changes in proximity with respect to the human body and closeness to fluids can create significant parasitic capacitance that can cause errors in pressure measurements. This is compensated for by using a capacitance measurement signal line that is not sensitive to pressure and only measures capacitance due to proximity to conductive bodies. The urodynamics application involves very sensitive pressure measurements, with required resolution of 0.1 psi or better. This high level of sensitivity is achieved in the sensor by using very small gaps between parallel electrodes, large electrode areas and special electrode shapes that significantly increase bending response of the sensing diaphragm.

Various force/contact-pressure sensing mechanisms could be explored for urethral pressure measurement. Piezoelectric sensors are not used in one embodiment since they do not measure static forces, and the pressure distribution to be measured in some embodiments is either static or varying very slowly in time. Piezoresistive sensors are not used in one embodiment since they are susceptible to drift and require calibration just before the measurement in order to be able to measure absolute pressures with accuracy. One embodiment uses a flexible capacitive sensing mechanism due to its high sensitivity for measuring low and static force/pressure with adequate resolution.

One embodiment is directed to a multi-sensor flexible catheter strip for measurement of distributed pressure inside the urethra. The sensor strip can be significantly bent during urethral insertion into the body. The sensor has important clinical applications in urodynamic testing and potentially in other in-vivo biomedical catheter applications. Capacitive force sensors were designed and micro-fabricated using surface micromachining, polyimide/PDMS substrates and copper electrodes. To remove the parasitic influence of urethral tissues which create fringe capacitance that can lead to significant errors, a reference fringe capacitance measurement sensor was incorporated on the strip. The sensing strip was embedded on a catheter and experimental in-vitro evaluation was conducted using a bench-top pressure chamber. The sensors on the strip were able to provide the required sensitivity and range. The experimental results also showed preliminary data to indicate that by using measurements from the reference parasitic sensor on the strip, the influence of human tissue parasitics on the urethral pressure measurements could be removed.

One embodiment is directed to a pressure sensing catheter system that includes a urethral catheter, and a sensor array formed on the urethral catheter. The sensor array includes a plurality of pressure sensors distributed along a length of the urethral catheter, and the sensor array is configured to produce a dynamic pressure distribution profile along a urethra. In one form of this embodiment, the sensor array includes at least one electromyography (EMG) electrode configured to perform EMG measurements in a urethra, wherein the at least one EMG electrode is configured to be positioned at a urogenital diaphragm of a patient. The sensor array is configured to provide concurrent measurement of pressures and EMG signals during provocative maneuvers.

In one embodiment, the pressure sensors are formed on a flexible strip that includes signal lines to carry signals from the pressure sensors to an external interface. The pressure sensors according to one embodiment are configured to measure pressures at least as low as 0.1 psi. In one embodiment, the pressure sensors are capacitive pressure sensors and each of the capacitive pressure sensors includes a top electrode and a bottom electrode separated by a gap, which is between about 0.1 µm to 100 µm in one embodiment. In one embodiment, the sensor array includes at least five pressure sensors, and the pressure sensors have a spacing between adjacent sensors of about 1 mm to 10 mm. The pressure sensors are spaced apart to cover a total length on the urethral catheter of about 3 cm to 5 cm.

In one embodiment, the sensor array includes a reference sensor that is substantially immune to pressure influence and is configured to measure parasitic capacitance caused by proximity to human tissue and produce a reference signal for compensating signals of the pressure sensors. The reference sensor according to one embodiment comprises a single electrode. In one embodiment, the sensor array comprises at least one piezoresistive transducer signal line to measure capacitance due to bending of the sensor array for compensating signals of the pressure sensors due to bending errors.

In one embodiment, each of the pressure sensors includes a top electrode formed on a top polyimide layer and a bottom electrode formed on a bottom polyimide layer, and the top electrode and the bottom electrode are separated by a gap. In one embodiment, each of the pressure sensors further includes a PolyDiMethylSiloxane (PDMS) spacer layer separating the top and bottom polyimide layers and the top and bottom electrodes.

Another embodiment is directed to a method of measuring pressure in a urethra. The method includes inserting a urethral catheter inside a urethra, wherein the urethral catheter includes a sensor array having a plurality of pressure sensors distributed along a length of the urethral catheter; measuring with each of the pressure sensors a value while the pressure sensor is being influenced by pressure within the urethra; and generating a dynamic pressure distribution profile along the urethra based on the values produced by the pressure sensors.

In one embodiment, the method of measuring pressure in a urethra further includes performing electromyography (EMG) measurements in the urethra using at least one EMG electrode formed on the sensor array, wherein the EMG measurements are performed concurrently with the measuring with each of the pressure sensors a value. In one embodiment, the pressure sensors are capacitive pressure sensors, and the method of measuring pressure in a urethra further includes measuring parasitic capacitance caused by proximity to human tissue using a reference sensor on the sensor array; and compensating signals produced by the capacitive pressure sensors based on the measured parasitic capacitance.

Yet another embodiment is directed to a pressure sensing catheter system that includes a Foley type catheter and a flexible sensor strip formed on the catheter, wherein the sensor strip includes a plurality of capacitive pressure sensors distributed along a length of the catheter, wherein the sensor strip includes signal lines to carry signals from the capacitive pressure sensors to an external interface, wherein the sensor strip includes at least one electromyography (EMG) electrode configured to perform EMG measurements in a urethra, and wherein the sensor strip is configured to produce a dynamic pressure distribution profile along the urethra.

In addition to the urological applications described above, the technology for distributed pressure sensors on a catheter has a number of other medical applications. Some examples of other applications where technology for an instrumented catheter would be valuable are:

(1) Muscle force measurement using measurement of intra-muscular pressure. This requires a pressure sensor inside a 25 gauge needle (smaller than the disclosed urethral catheter). The muscle force sensor has applications in multiple sclerosis, myasthenia, ALS, and other neuromuscular diseases.

(2) Measurement of pressure and tissue stiffness in muscle compartments to prevent compartment syndrome during extremity trauma.

(3) Measurement of pressure in the heart or cardiovascular system.

(4) Anorectal physiologic studies.

(5) Upper GI studies.

What is claimed is:

1. A pressure sensing catheter system, comprising:
   a urethral catheter; and
   a flexible sensor strip formed on the urethral catheter, wherein the flexible sensor strip includes a plurality of capacitive pressure sensors distributed along a length of the urethral catheter and includes signal lines to carry signals from the capacitive pressure sensors to an external interface.

2. The pressure sensing catheter system of claim 1, wherein the flexible sensor strip includes at least one electromyography (EMG) electrode configured to perform EMG measurements in a urethra.

3. The pressure sensing catheter system of claim 2, wherein the at least one EMG electrode is configured to be positioned at a urogenital diaphragm of a patient.

4. The pressure sensing catheter system of claim 2, wherein the flexible sensor strip is configured to provide concurrent measurement of pressures and EMG signals during provocative maneuvers.

5. The pressure sensing catheter system of claim 1, wherein the pressure sensors are configured to measure pressures at least as low as 0.1 psi.

6. The pressure sensing catheter system of claim 1, wherein each of the pressure sensors includes a top electrode and a bottom electrode separated by a gap.

7. The pressure sensing catheter system of claim 6, wherein the gap is between 0.1 µm to 100 µm.

8. The pressure sensing catheter system of claim 1, wherein the flexible sensor strip includes at least five capacitive pressure sensors.

9. The pressure sensing catheter system of claim 8, where the pressure sensors have a spacing between adjacent sensors of 1 mm to 10 mm.

10. The pressure sensing catheter system of claim 8, wherein the pressure sensors are spaced apart to cover a total length on the urethral catheter of 3 cm to 5 cm.

11. The pressure sensing catheter system of claim 1, wherein the flexible sensor strip includes a reference sensor that is immune to pressure influence and is configured to measure parasitic capacitance caused by proximity to human tissue and produce a reference signal for compensating signals of the pressure sensors.

12. The pressure sensing catheter system of claim 1, wherein the reference sensor comprises a single electrode.

13. The pressure sensing catheter system of claim 1, wherein the flexible sensor strip comprises at least one piezoresistive transducer signal line to measure capacitance due to bending of the flexible sensor strip for compensating signals of the pressure sensors due to bending errors.

14. The pressure sensing catheter system of claim 1, wherein each of the pressure sensors includes a top electrode formed on a top polyimide layer and a bottom electrode formed on a bottom polyimide layer, and wherein the top electrode and the bottom electrode are separated by a gap.

15. The pressure sensing catheter system of claim 14, wherein each of the pressure sensors further includes a PolyDiMethylSiloxane (PDMS) spacer layer separating the top and bottom polyimide layers and the top and bottom electrodes.

16. A method of measuring pressure in a urethra, comprising:
   inserting a urethral catheter inside a urethra, wherein the urethral catheter includes a flexible sensor strip having a plurality of capacitive pressure sensors distributed along a length of the urethral catheter and having signal lines to carry signals from the capacitive pressure sensors to an external interface;
   measuring with each of the capacitive pressure sensors a value while the capacitive pressure sensor is being influenced by pressure within the urethra; and
   generating a dynamic pressure distribution profile along the urethra based on the values produced by the capacitive pressure sensors.

17. The method of claim 16, and further comprising:
   performing electromyography (EMG) measurements in the urethra using at least one EMG electrode formed on the flexible sensor strip, wherein the EMG measurements are performed concurrently with the measuring with each of the pressure sensors a value.

18. The method of claim 16, wherein the method further comprises:
   measuring parasitic capacitance caused by proximity to human tissue using a reference sensor on the flexible sensor strip; and
   compensating signals produced by the capacitive pressure sensors based on the measured parasitic capacitance.

19. The method of claim 16, and further comprising:
   measuring, using at least one piezoresistive transducer signal line on the flexible sensor strip, capacitance due to bending of the flexible sensor strip for compensating signals of the capacitive pressure sensors due to bending errors.

20. A pressure sensing catheter system, comprising:
   a Foley type catheter; and
   a flexible sensor strip formed on the catheter, wherein the sensor strip includes a plurality of capacitive pressure sensors distributed along a length of the catheter, wherein the sensor strip includes signal lines to carry signals from the capacitive pressure sensors to an external interface, wherein the sensor strip includes at least one electromyography (EMG) electrode configured to perform EMG measurements in a urethra.

* * * * *